(12) United States Patent
Patton et al.

(10) Patent No.: US 6,300,091 B1
(45) Date of Patent: Oct. 9, 2001

(54) HERBICIDE TARGET GENES AND METHODS

(75) Inventors: David A. Patton, Durham, NC (US); Carl S. Ashby, Boulder, CO (US); John A. McElver, Durham, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/503,391

(22) Filed: Feb. 14, 2000

Related U.S. Application Data

(60) Provisional application No. 60/229,353, filed on Mar. 5, 1999, now abandoned, provisional application No. 60/228,817, filed on Jun. 8, 1999, now abandoned, and provisional application No. 60/198,213, filed on Sep. 29, 1999, now abandoned.

(51) Int. Cl.$^7$ .................................................. C12Q 1/48
(52) U.S. Cl. ............................................. 435/15; 435/193
(58) Field of Search ....................................... 435/15, 193

(56) References Cited

FOREIGN PATENT DOCUMENTS

| WO 95 16913 | 6/1995 | (WO) . |
| WO 97 27285 | 7/1997 | (WO) . |

OTHER PUBLICATIONS

Vollack et al. Acession T10247; S42477. (Alignment No. 1), Jul. 16, 1998.*
Patton et al., Molecular & General Genetics, vol. 227, No. 3, pp. 337–347 (1991).
Chen, et al., EMBL Sequence Data Library, Heidelberg, Germany, Accession No. AI997215, Sep. 9, 1999.
Feng et al., EMBL Sequence Data Library, Heidelberg, Germany, Accession No. B10372, May 16, 1997.
Topping et al., Development, vol. 124, pp. 4415–4424 (1997).
Abell et al., Weed Science, US, Weed Science Society of America, Champaign, IL, vol. 44, pp. 734–742 (1996).
International Search Report, PCT/US97/01384, pp. 1–2 (Apr. 1997).
Bar–Peled et al., The Plant Cell, 7:667–676 (1995).
Castle et al., Mol. Gen. Genet., 241:504–514 (1993).
Chen, C–Y. and Graham, T. R., "An arf1 Synthetic Lethal Screen Identifies a New Clathrin Heavy Chain Conditional Allel That Perturbs Vacuolar Protein Transport in Saccharomyces cerevisiae," Genetics, 150:577–589 (1998).
Clark et. al., Proc. Natl. Acad. Sci. A., 90 (19):8952–8956 (1993).
Errampalli et. al., The Plant Cell, 3:149–157 (1991).
Fukao et. al., J. Biochem, 106:197–204 (1989).
Fukao et. al., J. Clin. Invest., 86:2086–2092 (1990).
Hermans et. al., Plant Mol. Biol., 10:323–330 (1988).
Hiser et. al., J. Biol. Chem., 269:31383–31389 (1994).
Hoesche et. al., Biochimica et Biophysica Acta, 1142:293–305 (1993).
Hoesche et. al., Biochimica et Biophysica Acta, 1171:201–204 (1992).
Jurgens et. al., The Company of Biologists Limited, Development Supplement 1, 27–38 (1991).
Koncz et. al., Proc. Natl. Acad. Sci. USA, 86:8467–8471 (1989).
Lee, F–J. S. et. al., "Characterization of an ADP–ribosylation Factor–like 1 Protein in Saccharomyces cerevisiae," Journal of Biological Chemistry, 272 (49):30998–31005 (1997).
Liu and Whittier, Genomics, 25:674–681 (1995).
Liu et. al., The Plant Journal, 8:457–463 (1995).
Luking et al., Critical Reviews in Biochemistry and Molecular Biology, 33:259–296 (1998).
Mayer et. al., Nature, 353:402–407 (1991).
Minet et. al., The Plant Journal, 2:417–422 (1992).
Napier et. al., Plant Mol. Biol., 20:549–554 (1992).
Regad et.al., ADP–ribosylation factor (Arf) genes, FEBS Lett., 25:133–136 (1993).
Tamkun, J. W. et. al., "The arflike gene encodes an essential GTP–binding protein in Drosophila," Proc. Natl. Acad. Sci. USA, 88:3120–3124 (1991).
Tsugeki et. al., The Plant Journal, 10:479–489 (1996).
Verwoert, I. I. G. S. et al., "A Zea mays GTP–binding protein of the ARF family compliments an *Escherichia coli* mutant with a temperature–sensitive malonyl–coenzyme A:acyl carrier protein transacylase," Plant Molecular Biology, 27:629–633 (1995).
Vollack and Bach, Plant Physiol., 111:1097–1107 (1996).
Wilson et. al., Nature, 368:32–38 (1994).

\* cited by examiner

*Primary Examiner*—Nashaat T. Nashed
*Assistant Examiner*—Christian L. Fronda
(74) *Attorney, Agent, or Firm*—J. Timothy Meigs; Edouard G. Lebel; Larry W. Stults

(57) ABSTRACT

The invention relates to genes isolated from Arabidopsis that code for proteins essential for normal plant development. The invention also includes the methods of using these proteins to discover new herbicides, based on the essentiality of the genes for normal growth and development. The invention can also be used in a screening assay to identify inhibitors that are potential herbicides. The invention is also applied to the development of herbicide tolerant plants, plant tissues, plant seeds, and plant cells.

1 Claim, No Drawings

SEQUENCE LISTING

```
<160> NUMBER OF SEQ ID NOS: 26

<210> SEQ ID NO 1
<211> LENGTH: 1656
<212> TYPE: DNA
<213> ORGANISM: Arabidopsis thaliana
<220> FEATURE:
<221> NAME/KEY: CDS
<222> LOCATION: (1)..(1656)

<400> SEQUENCE: 1 atg gcg gca tca act tca acc cga ttc ctt gtt ctg ctc aaa gat ttt      48
Met Ala Ala Ser Thr Ser Thr Arg Phe Leu Val Leu Leu Lys Asp Phe
 1               5                  10                  15 tct gcc ttc aga aag ata tca tgg act tgt gct gca act aat ttt cac      96
Ser Ala Phe Arg Lys Ile Ser Trp Thr Cys Ala Ala Thr Asn Phe His
            20                  25                  30 cgc caa tct cgt ttt tta tgc cat gtt gcg aaa gaa gac ggg tct ctt     144
Arg Gln Ser Arg Phe Leu Cys His Val Ala Lys Glu Asp Gly Ser Leu
        35                  40                  45 act ctt gca agc ctt gat ttg ggg aac aaa cca cgg aaa ttt ggg aag     192
Thr Leu Ala Ser Leu Asp Leu Gly Asn Lys Pro Arg Lys Phe Gly Lys
    50                  55                  60 ggt aag gcg atg aag ctt gag gga agt ttt gtt act gaa atg ggt caa     240
Gly Lys Ala Met Lys Leu Glu Gly Ser Phe Val Thr Glu Met Gly Gln
65                  70                  75                  80 ggt aag gta aga gcg gta aag aac gat aaa atg aaa gtt gtc aag gaa     288
Gly Lys Val Arg Ala Val Lys Asn Asp Lys Met Lys Val Val Lys Glu
                85                  90                  95 aaa aag cca gct gag ata gtg tct cct ttg ttt tct gca aaa tcc ttt     336
Lys Lys Pro Ala Glu Ile Val Ser Pro Leu Phe Ser Ala Lys Ser Phe
            100                 105                 110 gag gag ctt ggc ctc ccg gat tcc ttg tta gac agt ttg gaa aga gaa     384
Glu Glu Leu Gly Leu Pro Asp Ser Leu Leu Asp Ser Leu Glu Arg Glu
        115                 120                 125 ggt ttc tct gtc cca aca gat gtc caa tca gca gct gtc ccg gca ata     432
Gly Phe Ser Val Pro Thr Asp Val Gln Ser Ala Ala Val Pro Ala Ile
    130                 135                 140 atc aaa ggt cac gat gca gtg att cag tct tac aca gga tct ggc aaa     480
Ile Lys Gly His Asp Ala Val Ile Gln Ser Tyr Thr Gly Ser Gly Lys
145                 150                 155                 160 aca tta gct tat ctg ctt cca ata ttg tcc gaa att ggt cct cta gca     528
```

```
                Thr Leu Ala Tyr Leu Leu Pro Ile Leu Ser Glu Ile Gly Pro Leu Ala
                                165                 170                 175 gaa aaa tct aga agt tcg cac agt gaa aat gat aag agg act gag att          576
Glu Lys Ser Arg Ser Ser His Ser Glu Asn Asp Lys Arg Thr Glu Ile
            180                 185                 190 cag gca atg atc gtg gct cca tca aga gaa ctc ggt atg cag ata gta          624
Gln Ala Met Ile Val Ala Pro Ser Arg Glu Leu Gly Met Gln Ile Val
        195                 200                 205 aga gag gta gag aaa ctg ctc gga cct gtt cac cgt aga atg gtt cag          672
Arg Glu Val Glu Lys Leu Leu Gly Pro Val His Arg Arg Met Val Gln
    210                 215                 220 cag ttg gta gga ggt gca aac cga atg agg caa gaa gag gcc ctt aag          720
Gln Leu Val Gly Gly Ala Asn Arg Met Arg Gln Glu Glu Ala Leu Lys
225                 230                 235                 240 aaa aat aaa cct gca att gtt gtt ggc act ccc ggg aga att gca gag          768
Lys Asn Lys Pro Ala Ile Val Val Gly Thr Pro Gly Arg Ile Ala Glu
                245                 250                 255 ata agc aaa ggt gga aaa ttg cac act cat ggg tgt aga ttc ttg gtg          816
Ile Ser Lys Gly Gly Lys Leu His Thr His Gly Cys Arg Phe Leu Val
            260                 265                 270 cta gac gaa gtc gat gag ctt tta tcg ttt aat ttc cga gaa gat atc          864
Leu Asp Glu Val Asp Glu Leu Leu Ser Phe Asn Phe Arg Glu Asp Ile
        275                 280                 285 cat cga ata cta gaa cat gta gga aag aga tct ggg gct ggt cct aaa          912
His Arg Ile Leu Glu His Val Gly Lys Arg Ser Gly Ala Gly Pro Lys
    290                 295                 300 gga gaa gtc gat gaa cgg gct aac cgg cag acc att cta gtc tct gca          960
Gly Glu Val Asp Glu Arg Ala Asn Arg Gln Thr Ile Leu Val Ser Ala
305                 310                 315                 320 act gtg cca ttc tcg gtt atc cga gca gct aaa agc tgg agt cac gag         1008
Thr Val Pro Phe Ser Val Ile Arg Ala Ala Lys Ser Trp Ser His Glu
                325                 330                 335 ccg gtt ctt gtc caa gcc aac aaa gtc act cct ctt gat acc gtt caa         1056
Pro Val Leu Val Gln Ala Asn Lys Val Thr Pro Leu Asp Thr Val Gln
            340                 345                 350 cca tct gca ccg gta atg agc ttg act ccc aca act tct gaa gct gat         1104
Pro Ser Ala Pro Val Met Ser Leu Thr Pro Thr Thr Ser Glu Ala Asp
        355                 360                 365 ggc cag att cag act act att cag agc tta cct cca gct tta aaa cac         1152
Gly Gln Ile Gln Thr Thr Ile Gln Ser Leu Pro Pro Ala Leu Lys His
    370                 375                 380 tat tac tgc atc tca aag cat caa cac aaa gtc gac acg tta agg aga         1200
Tyr Tyr Cys Ile Ser Lys His Gln His Lys Val Asp Thr Leu Arg Arg
385                 390                 395                 400 tgc gtt cac gcc ctc gat gcc caa tcg gtt ata gct ttc atg aac cac         1248
Cys Val His Ala Leu Asp Ala Gln Ser Val Ile Ala Phe Met Asn His
                405                 410                 415 tca agg cag ctc aaa gat gtg gtc tac aaa ctc gaa gct cgt ggt atg         1296
Ser Arg Gln Leu Lys Asp Val Val Tyr Lys Leu Glu Ala Arg Gly Met
            420                 425                 430 aat tca gct gag atg cac gga gat ctc ggg aag cta ggg aga tca aca         1344
Asn Ser Ala Glu Met His Gly Asp Leu Gly Lys Leu Gly Arg Ser Thr
        435                 440                 445 gtt cta aag aag ttc aag aac ggg gaa atc aag gta ctt gtg aca aac         1392
Val Leu Lys Lys Phe Lys Asn Gly Glu Ile Lys Val Leu Val Thr Asn
    450                 455                 460 gag ctc tct gcc cgg ggt ctg gat gtt gcg gaa tgt gat ctg gtg gtg         1440
Glu Leu Ser Ala Arg Gly Leu Asp Val Ala Glu Cys Asp Leu Val Val
465                 470                 475                 480
```

-continued

```
aat ctt gag ctt cca act gat gcg gtt cac tat gct cat cga gct ggg    1488
Asn Leu Glu Leu Pro Thr Asp Ala Val His Tyr Ala His Arg Ala Gly
            485                 490                 495 aga aca ggg agg ctg gga agg aaa ggg acg gtg gta aca gtg tgc gag    1536
Arg Thr Gly Arg Leu Gly Arg Lys Gly Thr Val Val Thr Val Cys Glu
        500                 505                 510 gaa tca caa gtg ttt ata gtg aag aag atg gag aag cag ctt ggt ttg    1584
Glu Ser Gln Val Phe Ile Val Lys Lys Met Glu Lys Gln Leu Gly Leu
    515                 520                 525 cct ttc ttg tat tgt gag ttt gtt gat gga gag ctt gtt gtc act gag    1632
Pro Phe Leu Tyr Cys Glu Phe Val Asp Gly Glu Leu Val Val Thr Glu
530                 535                 540 gaa gat aaa gct att ata agg tga                                    1656
Glu Asp Lys Ala Ile Ile Arg
545                 550
```

<210> SEQ ID NO 2
<211> LENGTH: 551
<212> TYPE: PRT
<213> ORGANISM: Arabidopsis thaliana

<400> SEQUENCE: 2

```
Met Ala Ala Ser Thr Ser Thr Arg Phe Leu Val Leu Leu Lys Asp Phe
  1               5                  10                  15

Ser Ala Phe Arg Lys Ile Ser Trp Thr Cys Ala Ala Thr Asn Phe His
             20                  25                  30

Arg Gln Ser Arg Phe Leu Cys His Val Ala Lys Glu Asp Gly Ser Leu
         35                  40                  45

Thr Leu Ala Ser Leu Asp Leu Gly Asn Lys Pro Arg Lys Phe Gly Lys
     50                  55                  60

Gly Lys Ala Met Lys Leu Glu Gly Ser Phe Val Thr Glu Met Gly Gln
 65                  70                  75                  80

Gly Lys Val Arg Ala Val Lys Asn Asp Lys Met Lys Val Val Lys Glu
                 85                  90                  95

Lys Lys Pro Ala Glu Ile Val Ser Pro Leu Phe Ser Ala Lys Ser Phe
            100                 105                 110

Glu Glu Leu Gly Leu Pro Asp Ser Leu Leu Asp Ser Leu Glu Arg Glu
        115                 120                 125

Gly Phe Ser Val Pro Thr Asp Val Gln Ser Ala Ala Val Pro Ala Ile
    130                 135                 140

Ile Lys Gly His Asp Ala Val Ile Gln Ser Tyr Thr Gly Ser Gly Lys
145                 150                 155                 160

Thr Leu Ala Tyr Leu Leu Pro Ile Leu Ser Glu Ile Gly Pro Leu Ala
                165                 170                 175

Glu Lys Ser Arg Ser Ser His Ser Glu Asn Asp Lys Arg Thr Glu Ile
            180                 185                 190

Gln Ala Met Ile Val Ala Pro Ser Arg Glu Leu Gly Met Gln Ile Val
        195                 200                 205

Arg Glu Val Glu Lys Leu Leu Gly Pro Val His Arg Arg Met Val Gln
    210                 215                 220

Gln Leu Val Gly Gly Ala Asn Arg Met Arg Gln Glu Glu Ala Leu Lys
225                 230                 235                 240

Lys Asn Lys Pro Ala Ile Val Val Gly Thr Pro Gly Arg Ile Ala Glu
                245                 250                 255

Ile Ser Lys Gly Gly Lys Leu His Thr His Gly Cys Arg Phe Leu Val
            260                 265                 270
```

-continued

Leu Asp Glu Val Asp Glu Leu Leu Ser Phe Asn Phe Arg Glu Asp Ile
         275                 280                 285

His Arg Ile Leu Glu His Val Gly Lys Arg Ser Gly Ala Gly Pro Lys
         290                 295             300

Gly Glu Val Asp Glu Arg Ala Asn Arg Gln Thr Ile Leu Val Ser Ala
305                 310                 315                 320

Thr Val Pro Phe Ser Val Ile Arg Ala Ala Lys Ser Trp Ser His Glu
             325                 330                 335

Pro Val Leu Val Gln Ala Asn Lys Val Thr Pro Leu Asp Thr Val Gln
         340                 345                 350

Pro Ser Ala Pro Val Met Ser Leu Thr Pro Thr Thr Ser Glu Ala Asp
         355                 360                 365

Gly Gln Ile Gln Thr Thr Ile Gln Ser Leu Pro Pro Ala Leu Lys His
370                 375                 380

Tyr Tyr Cys Ile Ser Lys His Gln His Lys Val Asp Thr Leu Arg Arg
385                 390                 395                 400

Cys Val His Ala Leu Asp Ala Gln Ser Val Ile Ala Phe Met Asn His
             405                 410                 415

Ser Arg Gln Leu Lys Asp Val Val Tyr Lys Leu Glu Ala Arg Gly Met
         420                 425                 430

Asn Ser Ala Glu Met His Gly Asp Leu Gly Lys Leu Gly Arg Ser Thr
         435                 440                 445

Val Leu Lys Lys Phe Lys Asn Gly Glu Ile Lys Val Leu Val Thr Asn
450                 455                 460

Glu Leu Ser Ala Arg Gly Leu Asp Val Ala Glu Cys Asp Leu Val Val
465                 470                 475                 480

Asn Leu Glu Leu Pro Thr Asp Ala Val His Tyr Ala His Arg Ala Gly
             485                 490                 495

Arg Thr Gly Arg Leu Gly Arg Lys Gly Thr Val Val Thr Val Cys Glu
         500                 505                 510

Glu Ser Gln Val Phe Ile Val Lys Lys Met Glu Lys Gln Leu Gly Leu
         515                 520                 525

Pro Phe Leu Tyr Cys Glu Phe Val Asp Gly Glu Leu Val Val Thr Glu
         530                 535                 540

Glu Asp Lys Ala Ile Ile Arg
545                 550

<210> SEQ ID NO 3
<211> LENGTH: 1997
<212> TYPE: DNA
<213> ORGANISM: Arabidopsis thaliana
<220> FEATURE:
<221> NAME/KEY: 5'UTR
<222> LOCATION: (1)..(271)
<220> FEATURE:
<221> NAME/KEY: CDS
<222> LOCATION: (272)..(1927)
<220> FEATURE:
<221> NAME/KEY: 3'UTR
<222> LOCATION: (1928)..(1997)

<400> SEQUENCE: 3
attttttgag tcggaacctg aagtatttta gtccgtttgt gataaagaaa accgagactg     60
taccggttta tcttcagacc cggttgtttg tccggtttgg taaaattaga acctaacctt    120
tttatccaga actggagact ttggaagaac tgtagaagtg ttgttctctt cgtatcgtcc    180
tcaatcctca tggagactat tatcaggctg ttttgagcaa acgctgtgat aaagaggctt    240

```
tctttcttgc tagcaagtac acacgagtga c atg gcg gca tca act tca acc      292
                                   Met Ala Ala Ser Thr Ser Thr
                                   1               5 cga ttc ctt gtt ctg ctc aaa gat ttt tct gcc ttc aga aag ata tca      340
Arg Phe Leu Val Leu Leu Lys Asp Phe Ser Ala Phe Arg Lys Ile Ser
        10                  15                  20 tgg act tgt gct gca act aat ttt cac cgc caa tct cgt ttt tta tgc      388
Trp Thr Cys Ala Ala Thr Asn Phe His Arg Gln Ser Arg Phe Leu Cys
    25                  30                  35 cat gtt gcg aaa gaa gac ggg tct ctt act ctt gca agc ctt gat ttg      436
His Val Ala Lys Glu Asp Gly Ser Leu Thr Leu Ala Ser Leu Asp Leu
40                  45                  50                  55 ggg aac aaa cca cgg aaa ttt ggg aag ggt aag gcg atg aag ctt gag      484
Gly Asn Lys Pro Arg Lys Phe Gly Lys Gly Lys Ala Met Lys Leu Glu
                60                  65                  70 gga agt ttt gtt act gaa atg ggt caa ggt aag gta aga gcg gta aag      532
Gly Ser Phe Val Thr Glu Met Gly Gln Gly Lys Val Arg Ala Val Lys
            75                  80                  85 aac gat aaa atg aaa gtt gtg aag gaa aaa aag cca gct gag ata gtg      580
Asn Asp Lys Met Lys Val Val Lys Glu Lys Lys Pro Ala Glu Ile Val
        90                  95                 100 tct cct ttg ttt tct gca aaa tcc ttt gag gag ctt ggc ctc ccg gat      628
Ser Pro Leu Phe Ser Ala Lys Ser Phe Glu Glu Leu Gly Leu Pro Asp
    105                 110                 115 tcc ttg tta gac agt ttg gaa aga gaa ggt ttc tct gtc cca aca gat      676
Ser Leu Leu Asp Ser Leu Glu Arg Glu Gly Phe Ser Val Pro Thr Asp
120                 125                 130                 135 gtc caa tca gca gct gtc ccg gca ata atc aaa ggt cac gat gca gtg      724
Val Gln Ser Ala Ala Val Pro Ala Ile Ile Lys Gly His Asp Ala Val
                140                 145                 150 att cag tct tac aca gga tct ggc aaa aca tta gct tat ctg ctt cca      772
Ile Gln Ser Tyr Thr Gly Ser Gly Lys Thr Leu Ala Tyr Leu Leu Pro
            155                 160                 165 ata ttg tcc gaa att ggt cct cta gca gaa aaa tct aga agt tcg cac      820
Ile Leu Ser Glu Ile Gly Pro Leu Ala Glu Lys Ser Arg Ser Ser His
        170                 175                 180 agt gaa aat gat aag agg act gag att cag gca atg atc gtg gct cca      868
Ser Glu Asn Asp Lys Arg Thr Glu Ile Gln Ala Met Ile Val Ala Pro
    185                 190                 195 tca aga gaa ctc ggt atg cag ata gta aga gag gta gag aaa ctg ctc      916
Ser Arg Glu Leu Gly Met Gln Ile Val Arg Glu Val Glu Lys Leu Leu
200                 205                 210                 215 gga cct gtt cac cgt aga atg gtt cag cag ttg gta gga ggt gca aac      964
Gly Pro Val His Arg Arg Met Val Gln Gln Leu Val Gly Gly Ala Asn
                220                 225                 230 cga atg agg caa gaa gag gcc ctt aag aaa aat aaa cct gca att gtt     1012
Arg Met Arg Gln Glu Glu Ala Leu Lys Lys Asn Lys Pro Ala Ile Val
            235                 240                 245 gtt ggc act ccc ggg aga att gca gag ata agc aaa ggt gga aaa ttg     1060
Val Gly Thr Pro Gly Arg Ile Ala Glu Ile Ser Lys Gly Gly Lys Leu
        250                 255                 260 cac act cat ggg tgt aga ttc ttg gtg cta gac gaa gtc gat gag ctt     1108
His Thr His Gly Cys Arg Phe Leu Val Leu Asp Glu Val Asp Glu Leu
    265                 270                 275 tta tcg ttt aat ttc cga gaa gat atc cat cga ata cta gaa cat gta     1156
Leu Ser Phe Asn Phe Arg Glu Asp Ile His Arg Ile Leu Glu His Val
280                 285                 290                 295 gga aag aga tct ggg gct ggt cct aaa gga gaa gtc gat gaa cgg gct     1204
Gly Lys Arg Ser Gly Ala Gly Pro Lys Gly Glu Val Asp Glu Arg Ala
                300                 305                 310
```

-continued

| | |
|---|---|
| aac cgg cag acc att cta gtc tct gca act gtg cca ttc tcg gtt atc<br>Asn Arg Gln Thr Ile Leu Val Ser Ala Thr Val Pro Phe Ser Val Ile<br>             315                      320                      325 | 1252 |
| cga gca gct aaa agc tgg agt cac gag cct gtt ctt gtc caa gcc aac<br>Arg Ala Ala Lys Ser Trp Ser His Glu Pro Val Leu Val Gln Ala Asn<br>          330                      335                      340 | 1300 |
| aaa gtc act cct ctt gat acc gtt caa cca tct gca ccg gta atg agc<br>Lys Val Thr Pro Leu Asp Thr Val Gln Pro Ser Ala Pro Val Met Ser<br>        345                      350                      355 | 1348 |
| ttg act ccc aca act tct gaa gct gat ggc cag att cag act act att<br>Leu Thr Pro Thr Thr Ser Glu Ala Asp Gly Gln Ile Gln Thr Thr Ile<br>360                      365                      370                      375 | 1396 |
| cag agc tta cct cca gct tta aaa cac tat tac tgc atc tca aag cat<br>Gln Ser Leu Pro Pro Ala Leu Lys His Tyr Tyr Cys Ile Ser Lys His<br>             380                      385                      390 | 1444 |
| caa cac aaa gtc gat acg tta agg aga tgc gtt cac gcc ctc gat gcc<br>Gln His Lys Val Asp Thr Leu Arg Arg Cys Val His Ala Leu Asp Ala<br>        395                      400                      405 | 1492 |
| caa tcg gtt ata gct ttc atg aac cac tca agg cag ctc aaa gat gtg<br>Gln Ser Val Ile Ala Phe Met Asn His Ser Arg Gln Leu Lys Asp Val<br>410                      415                      420 | 1540 |
| gtc tac aaa ctc gaa gct cgt ggt atg aat tca gct gag atg cac gga<br>Val Tyr Lys Leu Glu Ala Arg Gly Met Asn Ser Ala Glu Met His Gly<br>        425                      430                      435 | 1588 |
| gat ctc ggg aag cta ggg aga tca aca gtt cta aag aag ttc aag aac<br>Asp Leu Gly Lys Leu Gly Arg Ser Thr Val Leu Lys Lys Phe Lys Asn<br>440                      445                      450                      455 | 1636 |
| ggg gaa atc aag gta ctt gtg aca aac gag ctc tct gct cgg ggt ctt<br>Gly Glu Ile Lys Val Leu Val Thr Asn Glu Leu Ser Ala Arg Gly Leu<br>             460                      465                      470 | 1684 |
| gat gtt gcg gaa tgt gat ctg gtg gtg aat ctt gag ctt cca act gat<br>Asp Val Ala Glu Cys Asp Leu Val Val Asn Leu Glu Leu Pro Thr Asp<br>             475                      480                      485 | 1732 |
| gcg gtt cac tat gct cat cga gct ggg aga aca ggg agg ctg gga agg<br>Ala Val His Tyr Ala His Arg Ala Gly Arg Thr Gly Arg Leu Gly Arg<br>        490                      495                      500 | 1780 |
| aaa ggg acg gtg gta aca gtg tgc gag gaa tca caa gtg ttt ata gtg<br>Lys Gly Thr Val Val Thr Val Cys Glu Glu Ser Gln Val Phe Ile Val<br>505                      510                      515 | 1828 |
| aag aag atg gag aag cag ctt ggt ttg cct ttc ttg tat tgt gag ttt<br>Lys Lys Met Glu Lys Gln Leu Gly Leu Pro Phe Leu Tyr Cys Glu Phe<br>520                      525                      530                      535 | 1876 |
| gtt gat gga gag ctt gtt gtc act gag gaa gat aaa gct att ata agg<br>Val Asp Gly Glu Leu Val Val Thr Glu Glu Asp Lys Ala Ile Ile Arg<br>             540                      545                      550 | 1924 |
| tga aaatctaaag atgtaatttt cagatactat tattactatt gaaaattcag | 1977 |
| agtcaaaaaa aaaaaaaaa | 1997 |

<210> SEQ ID NO 4
<211> LENGTH: 551
<212> TYPE: PRT
<213> ORGANISM: Arabidopsis thaliana

<400> SEQUENCE: 4

Met Ala Ala Ser Thr Ser Thr Arg Phe Leu Val Leu Leu Lys Asp Phe
  1               5                  10               15

Ser Ala Phe Arg Lys Ile Ser Trp Thr Cys Ala Ala Thr Asn Phe His
             20                  25               30

-continued

```
Arg Gln Ser Arg Phe Leu Cys His Val Ala Lys Glu Asp Gly Ser Leu
        35                  40                  45

Thr Leu Ala Ser Leu Asp Leu Gly Asn Lys Pro Arg Lys Phe Gly Lys
     50                  55                  60

Gly Lys Ala Met Lys Leu Glu Gly Ser Phe Val Thr Glu Met Gly Gln
 65              70                  75                      80

Gly Lys Val Arg Ala Val Lys Asn Asp Lys Met Lys Val Val Lys Glu
                85                  90                  95

Lys Lys Pro Ala Glu Ile Val Ser Pro Leu Phe Ser Ala Lys Ser Phe
            100                 105                 110

Glu Glu Leu Gly Leu Pro Asp Ser Leu Leu Asp Ser Leu Glu Arg Glu
            115                 120                 125

Gly Phe Ser Val Pro Thr Asp Val Gln Ser Ala Ala Val Pro Ala Ile
        130                 135                 140

Ile Lys Gly His Asp Ala Val Ile Gln Ser Tyr Thr Gly Ser Gly Lys
145                 150                 155                 160

Thr Leu Ala Tyr Leu Leu Pro Ile Leu Ser Glu Ile Gly Pro Leu Ala
                165                 170                 175

Glu Lys Ser Arg Ser Ser His Ser Glu Asn Asp Lys Arg Thr Glu Ile
            180                 185                 190

Gln Ala Met Ile Val Ala Pro Ser Arg Glu Leu Gly Met Gln Ile Val
        195                 200                 205

Arg Glu Val Glu Lys Leu Leu Gly Pro Val His Arg Arg Met Val Gln
    210                 215                 220

Gln Leu Val Gly Gly Ala Asn Arg Met Arg Gln Glu Glu Ala Leu Lys
225                 230                 235                 240

Lys Asn Lys Pro Ala Ile Val Val Gly Thr Pro Gly Arg Ile Ala Glu
                245                 250                 255

Ile Ser Lys Gly Gly Lys Leu His Thr His Gly Cys Arg Phe Leu Val
            260                 265                 270

Leu Asp Glu Val Asp Glu Leu Leu Ser Phe Asn Phe Arg Glu Asp Ile
        275                 280                 285

His Arg Ile Leu Glu His Val Gly Lys Arg Ser Gly Ala Gly Pro Lys
    290                 295                 300

Gly Glu Val Asp Glu Arg Ala Asn Arg Gln Thr Ile Leu Val Ser Ala
305                 310                 315                 320

Thr Val Pro Phe Ser Val Ile Arg Ala Ala Lys Ser Trp Ser His Glu
                325                 330                 335

Pro Val Leu Val Gln Ala Asn Lys Val Thr Pro Leu Asp Thr Val Gln
            340                 345                 350

Pro Ser Ala Pro Val Met Ser Leu Thr Pro Thr Thr Ser Glu Ala Asp
        355                 360                 365

Gly Gln Ile Gln Thr Thr Ile Gln Ser Leu Pro Pro Ala Leu Lys His
    370                 375                 380

Tyr Tyr Cys Ile Ser Lys His Gln His Lys Val Asp Thr Leu Arg Arg
385                 390                 395                 400

Cys Val His Ala Leu Asp Ala Gln Ser Val Ile Ala Phe Met Asn His
                405                 410                 415

Ser Arg Gln Leu Lys Asp Val Val Tyr Lys Leu Glu Ala Arg Gly Met
            420                 425                 430

Asn Ser Ala Glu Met His Gly Asp Leu Gly Lys Leu Gly Arg Ser Thr
        435                 440                 445

Val Leu Lys Lys Phe Lys Asn Gly Glu Ile Lys Val Leu Val Thr Asn
```

```
                 450                 455                 460
Glu Leu Ser Ala Arg Gly Leu Asp Val Ala Glu Cys Asp Leu Val Val
465                 470                 475                 480

Asn Leu Glu Leu Pro Thr Asp Ala Val His Tyr Ala His Arg Ala Gly
                485                 490                 495

Arg Thr Gly Arg Leu Gly Arg Lys Gly Thr Val Val Thr Val Cys Glu
            500                 505                 510

Glu Ser Gln Val Phe Ile Val Lys Lys Met Glu Lys Gln Leu Gly Leu
        515                 520                 525

Pro Phe Leu Tyr Cys Glu Phe Val Asp Gly Glu Leu Val Val Thr Glu
    530                 535                 540

Glu Asp Lys Ala Ile Ile Arg
545                 550

<210> SEQ ID NO 5
<211> LENGTH: 558
<212> TYPE: DNA
<213> ORGANISM: Arabidopsis thaliana
<220> FEATURE:
<221> NAME/KEY: CDS
<222> LOCATION: (1)..(558)

<400> SEQUENCE: 5 atg gga ctg tta agc ata atc cgg aag atc aag aag aaa gag aag gag        48
Met Gly Leu Leu Ser Ile Ile Arg Lys Ile Lys Lys Lys Glu Lys Glu
  1               5                  10                  15 atg cgt att ctt atg gtt gga ctt gat aat tct ggg aag acg acg att        96
Met Arg Ile Leu Met Val Gly Leu Asp Asn Ser Gly Lys Thr Thr Ile
             20                  25                  30 gtt ctg aaa ata aac gga gaa gac aca agt gtg att agt cca act ctt       144
Val Leu Lys Ile Asn Gly Glu Asp Thr Ser Val Ile Ser Pro Thr Leu
         35                  40                  45 gga ttc aac atc aaa acc att atc tac caa aag tat acg cta aat ata       192
Gly Phe Asn Ile Lys Thr Ile Ile Tyr Gln Lys Tyr Thr Leu Asn Ile
     50                  55                  60 tgg gat gtt ggt ggg caa aag act ata aga tcg tat tgg agg aat tac       240
Trp Asp Val Gly Gly Gln Lys Thr Ile Arg Ser Tyr Trp Arg Asn Tyr
 65                  70                  75                  80 ttt gag cag act gat ggt ttg gtt tgg gtg gtt gat agt tct gat ctt       288
Phe Glu Gln Thr Asp Gly Leu Val Trp Val Val Asp Ser Ser Asp Leu
                 85                  90                  95 agg agg tta gat gat tgc aag atg gaa ctt gac aat ctc ttg aaa gaa       336
Arg Arg Leu Asp Asp Cys Lys Met Glu Leu Asp Asn Leu Leu Lys Glu
            100                 105                 110 gag agg cta gct ggt tca tct ttg ctg ata cta gca aat aag cag gat       384
Glu Arg Leu Ala Gly Ser Ser Leu Leu Ile Leu Ala Asn Lys Gln Asp
        115                 120                 125 att caa ggt gca cta aca cct gat gaa att ggc aag gtg cta aac tta       432
Ile Gln Gly Ala Leu Thr Pro Asp Glu Ile Gly Lys Val Leu Asn Leu
    130                 135                 140 gag tcc atg gat aaa agc cgg cac tgg aag ata gtg ggt tgc agc gca       480
Glu Ser Met Asp Lys Ser Arg His Trp Lys Ile Val Gly Cys Ser Ala
145                 150                 155                 160 tac acg ggt gaa ggt ttg ttg gaa gga ttc gat tgg ttg gtt caa gac       528
Tyr Thr Gly Glu Gly Leu Leu Glu Gly Phe Asp Trp Leu Val Gln Asp
                165                 170                 175 att gcc tcc agg att tac atg ctt gac taa                               558
Ile Ala Ser Arg Ile Tyr Met Leu Asp
                180                 185
```

-continued

```
<210> SEQ ID NO 6
<211> LENGTH: 185
<212> TYPE: PRT
<213> ORGANISM: Arabidopsis thaliana

<400> SEQUENCE: 6

Met Gly Leu Leu Ser Ile Ile Arg Lys Ile Lys Lys Glu Lys Glu
 1               5                  10                  15

Met Arg Ile Leu Met Val Gly Leu Asp Asn Ser Gly Lys Thr Thr Ile
                20                  25                  30

Val Leu Lys Ile Asn Gly Glu Asp Thr Ser Val Ile Ser Pro Thr Leu
            35                  40                  45

Gly Phe Asn Ile Lys Thr Ile Ile Tyr Gln Lys Tyr Thr Leu Asn Ile
        50                  55                  60

Trp Asp Val Gly Gly Gln Lys Thr Ile Arg Ser Tyr Trp Arg Asn Tyr
 65                  70                  75                  80

Phe Glu Gln Thr Asp Gly Leu Val Trp Val Val Asp Ser Ser Asp Leu
                85                  90                  95

Arg Arg Leu Asp Asp Cys Lys Met Glu Leu Asp Asn Leu Leu Lys Glu
            100                 105                 110

Glu Arg Leu Ala Gly Ser Ser Leu Leu Ile Leu Ala Asn Lys Gln Asp
        115                 120                 125

Ile Gln Gly Ala Leu Thr Pro Asp Glu Ile Gly Lys Val Leu Asn Leu
    130                 135                 140

Glu Ser Met Asp Lys Ser Arg His Trp Lys Ile Val Gly Cys Ser Ala
145                 150                 155                 160

Tyr Thr Gly Glu Gly Leu Leu Glu Gly Phe Asp Trp Leu Val Gln Asp
                165                 170                 175

Ile Ala Ser Arg Ile Tyr Met Leu Asp
            180                 185

<210> SEQ ID NO 7
<211> LENGTH: 1212
<212> TYPE: DNA
<213> ORGANISM: Arabidopsis thaliana
<220> FEATURE:
<221> NAME/KEY: CDS
<222> LOCATION: (1)..(1212)

<400> SEQUENCE: 7 atg gcc cat aca tca gaa tct gtg aat cct aga gat gtt tgc att gtg    48
Met Ala His Thr Ser Glu Ser Val Asn Pro Arg Asp Val Cys Ile Val
 1               5                  10                  15 ggt gtt gca cgt act cca atg ggt ggc ttt ctc gga tct ctt tca tct    96
Gly Val Ala Arg Thr Pro Met Gly Gly Phe Leu Gly Ser Leu Ser Ser
                20                  25                  30 tta cct gcc aca aag ctt gga tct tta gct att gca gct gct ttg aag   144
Leu Pro Ala Thr Lys Leu Gly Ser Leu Ala Ile Ala Ala Ala Leu Lys
            35                  40                  45 aga gca aat gtt gat cca gct ctt gtt caa gaa gtt gtc ttt ggc aat   192
Arg Ala Asn Val Asp Pro Ala Leu Val Gln Glu Val Val Phe Gly Asn
        50                  55                  60 gtt ctt agt gct aat ttg ggt caa gct cct gct cgt caa gct gct tta   240
Val Leu Ser Ala Asn Leu Gly Gln Ala Pro Ala Arg Gln Ala Ala Leu
 65                  70                  75                  80 ggt gca gga atc cct aac tct gtt atc tgt act aca gtt aac aag gtt   288
Gly Ala Gly Ile Pro Asn Ser Val Ile Cys Thr Thr Val Asn Lys Val
                85                  90                  95
```

-continued

| | | |
|---|---|---|
| tgt gca tca ggc atg aaa gcg gta atg att gct gct caa agt atc cag<br>Cys Ala Ser Gly Met Lys Ala Val Met Ile Ala Ala Gln Ser Ile Gln<br>100                                    105                          110 | 336 |
| tta ggg atc aat gat gta gtt gtg gcg ggt ggt atg gaa agc atg tct<br>Leu Gly Ile Asn Asp Val Val Ala Gly Gly Met Glu Ser Met Ser<br>        115                           120                        125 | 384 |
| aat aca cca aaa tat ttg gca gaa gca agg aag gga tct cgt ttt ggt<br>Asn Thr Pro Lys Tyr Leu Ala Glu Ala Arg Lys Gly Ser Arg Phe Gly<br>130                                 135                        140 | 432 |
| cat gat tct tta gta gat gga atg ttg aag gat gga cta tgg gat gtc<br>His Asp Ser Leu Val Asp Gly Met Leu Lys Asp Gly Leu Trp Asp Val<br>145                               150                           155                        160 | 480 |
| tat aac gac tgt ggg atg gga agc tgt gca gaa tta tgc gct gag aag<br>Tyr Asn Asp Cys Gly Met Gly Ser Cys Ala Glu Leu Cys Ala Glu Lys<br>                        165                           170                        175 | 528 |
| ttt cag att aca agg gag cag caa gat gac tat gca gtt cag agt ttt<br>Phe Gln Ile Thr Arg Glu Gln Gln Asp Asp Tyr Ala Val Gln Ser Phe<br>                 180                           185                        190 | 576 |
| gag cgt ggt att gct gcc cag gaa gct ggc gcc ttc aca tgg gaa atc<br>Glu Arg Gly Ile Ala Ala Gln Glu Ala Gly Ala Phe Thr Trp Glu Ile<br>                        195                           200                        205 | 624 |
| gtc ccg gtt gaa gtt tct gga gga aga ggt agg cca tca acc att gtt<br>Val Pro Val Glu Val Ser Gly Gly Arg Gly Arg Pro Ser Thr Ile Val<br>210                                 215                        220 | 672 |
| gac aag gac gaa ggt ctt ggg aag ttt gat gct gca aaa ttg agg aaa<br>Asp Lys Asp Glu Gly Leu Gly Lys Phe Asp Ala Ala Lys Leu Arg Lys<br>225                               230                           235                        240 | 720 |
| ctc cgt cct agt ttc aaa gag aat gga ggg act gtt aca gct gga aat<br>Leu Arg Pro Ser Phe Lys Glu Asn Gly Gly Thr Val Thr Ala Gly Asn<br>                        245                           250                        255 | 768 |
| gcg tct agc ata agt gat ggt gca gct gcc ctt gtc cta gtg agc gga<br>Ala Ser Ser Ile Ser Asp Gly Ala Ala Ala Leu Val Leu Val Ser Gly<br>                 260                           265                        270 | 816 |
| gag aag gct ctt cag cta gga ctt cta gta tta gca aaa att aaa ggg<br>Glu Lys Ala Leu Gln Leu Gly Leu Leu Val Leu Ala Lys Ile Lys Gly<br>                275                           280                        285 | 864 |
| tat ggt gac gca gct cag gaa cca gag ttt ttc act act gct cct gct<br>Tyr Gly Asp Ala Ala Gln Glu Pro Glu Phe Phe Thr Thr Ala Pro Ala<br>290                                 295                        300 | 912 |
| ctt gct ata cca aaa gcc att gca cat gct ggt ttg gaa tct tct caa<br>Leu Ala Ile Pro Lys Ala Ile Ala His Ala Gly Leu Glu Ser Ser Gln<br>305                               310                           315                        320 | 960 |
| gtt gat tac tat gag atc aat gaa gca ttt gca gtt gta gca ctt gca<br>Val Asp Tyr Tyr Glu Ile Asn Glu Ala Phe Ala Val Val Ala Leu Ala<br>                        325                           330                        335 | 1008 |
| aat caa aag cta ctc ggg att gct cca gag aaa gtg aac gta aat gga<br>Asn Gln Lys Leu Leu Gly Ile Ala Pro Glu Lys Val Asn Val Asn Gly<br>                 340                           345                        350 | 1056 |
| gga gct gtc tcc tta gga cac cct cta ggc tgc agt ggc gcc cgt att<br>Gly Ala Val Ser Leu Gly His Pro Leu Gly Cys Ser Gly Ala Arg Ile<br>                355                           360                        365 | 1104 |
| cta atc acg ttg ctt ggg ata cta aag aag aga aac gga aag tac ggt<br>Leu Ile Thr Leu Leu Gly Ile Leu Lys Lys Arg Asn Gly Lys Tyr Gly<br>              370                           375                        380 | 1152 |
| gtg gga gga gtg tgc aac gga gga gga ggt gct tct gct cta gtt ctt<br>Val Gly Gly Val Cys Asn Gly Gly Gly Gly Ala Ser Ala Leu Val Leu<br>385                               390                           395                        400 | 1200 |
| gag ctc ctt tga<br>Glu Leu Leu | 1212 |

```
<210> SEQ ID NO 8
<211> LENGTH: 403
<212> TYPE: PRT
<213> ORGANISM: Arabidopsis thaliana

<400> SEQUENCE: 8

Met Ala His Thr Ser Glu Ser Val Asn Pro Arg Asp Val Cys Ile Val
  1               5                  10                  15

Gly Val Ala Arg Thr Pro Met Gly Gly Phe Leu Gly Ser Leu Ser Ser
                 20                  25                  30

Leu Pro Ala Thr Lys Leu Gly Ser Leu Ala Ile Ala Ala Ala Leu Lys
             35                  40                  45

Arg Ala Asn Val Asp Pro Ala Leu Val Gln Glu Val Phe Gly Asn
         50                  55                  60

Val Leu Ser Ala Asn Leu Gly Gln Ala Pro Ala Arg Gln Ala Ala Leu
 65                  70                  75                  80

Gly Ala Gly Ile Pro Asn Ser Val Ile Cys Thr Thr Val Asn Lys Val
                 85                  90                  95

Cys Ala Ser Gly Met Lys Ala Val Met Ile Ala Ala Gln Ser Ile Gln
                100                 105                 110

Leu Gly Ile Asn Asp Val Val Ala Gly Gly Met Glu Ser Met Ser
            115                 120                 125

Asn Thr Pro Lys Tyr Leu Ala Glu Ala Arg Lys Gly Ser Arg Phe Gly
    130                 135                 140

His Asp Ser Leu Val Asp Gly Met Leu Lys Asp Gly Leu Trp Asp Val
145                 150                 155                 160

Tyr Asn Asp Cys Gly Met Gly Ser Cys Ala Glu Leu Cys Ala Glu Lys
                165                 170                 175

Phe Gln Ile Thr Arg Glu Gln Gln Asp Asp Tyr Ala Val Gln Ser Phe
            180                 185                 190

Glu Arg Gly Ile Ala Ala Gln Glu Ala Gly Ala Phe Thr Trp Glu Ile
        195                 200                 205

Val Pro Val Glu Val Ser Gly Gly Arg Gly Arg Pro Ser Thr Ile Val
    210                 215                 220

Asp Lys Asp Glu Gly Leu Gly Lys Phe Asp Ala Ala Lys Leu Arg Lys
225                 230                 235                 240

Leu Arg Pro Ser Phe Lys Glu Asn Gly Gly Thr Val Thr Ala Gly Asn
                245                 250                 255

Ala Ser Ser Ile Ser Asp Gly Ala Ala Ala Leu Val Leu Val Ser Gly
            260                 265                 270

Glu Lys Ala Leu Gln Leu Gly Leu Leu Val Leu Ala Lys Ile Lys Gly
        275                 280                 285

Tyr Gly Asp Ala Ala Gln Glu Pro Glu Phe Phe Thr Thr Ala Pro Ala
    290                 295                 300

Leu Ala Ile Pro Lys Ala Ile Ala His Ala Gly Leu Glu Ser Ser Gln
305                 310                 315                 320

Val Asp Tyr Tyr Glu Ile Asn Glu Ala Phe Ala Val Ala Leu Ala
                325                 330                 335

Asn Gln Lys Leu Leu Gly Ile Ala Pro Glu Lys Val Asn Val Asn Gly
            340                 345                 350

Gly Ala Val Ser Leu Gly His Pro Leu Gly Cys Ser Gly Ala Arg Ile
        355                 360                 365

Leu Ile Thr Leu Leu Gly Ile Leu Lys Lys Arg Asn Gly Lys Tyr Gly
    370                 375                 380
```

Val Gly Gly Val Cys Asn Gly Gly Gly Gly Ala Ser Ala Leu Val Leu
385                 390                 395                 400

Glu Leu Leu

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ngtcgaswga nawgaa                                                16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tgwgnagsan casaga                                                16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
agwgnagwan cawagg                                                16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
sttgntastn ctntgc                                                16

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ntcgastwts gwgtt                                                 15

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 14
wgtgnagwan canaga                                               16

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
attaggcacc ccaggcttta cactttatg                                 29

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
gtatgttgtg tggaattgtg agcggataac                                30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
taacaatttc acacaggaaa cagctatgac                                30

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
tagcatctga atttcataac caatctcgat acac                           34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
gcttcctatt atatcttccc aaattaccaa taca                           34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 20
gccttttcag aaatggataa atagccttgc ttcc                                34

<210> SEQ ID NO 21
<211> LENGTH: 705
<212> TYPE: DNA
<213> ORGANISM: Arabidopsis thaliana
<220> FEATURE:
<221> NAME/KEY: CDS
<222> LOCATION: (1)..(705)

<400> SEQUENCE: 21 atg gcg tct ctt caa caa act cta ttc tct ctt caa tcc aaa ctc cca     48
Met Ala Ser Leu Gln Gln Thr Leu Phe Ser Leu Gln Ser Lys Leu Pro
 1               5                  10                  15 cca tcc tcc ttc caa atc gcc aga tct ctc cca ctc cga aaa acc ttc     96
Pro Ser Ser Phe Gln Ile Ala Arg Ser Leu Pro Leu Arg Lys Thr Phe
             20                  25                  30 cca atc cga atc aac aac ggt gga aac gcc gcc gga gca aga atg tca    144
Pro Ile Arg Ile Asn Asn Gly Gly Asn Ala Ala Gly Ala Arg Met Ser
         35                  40                  45 gcc acc gca gca tca agc tac gcg atg gca tta gca gac gtc gcg aaa    192
Ala Thr Ala Ala Ser Ser Tyr Ala Met Ala Leu Ala Asp Val Ala Lys
     50                  55                  60 aga aac gac aca atg gaa tta aca gtc aca gac atc gag aag ctc gaa    240
Arg Asn Asp Thr Met Glu Leu Thr Val Thr Asp Ile Glu Lys Leu Glu
 65                  70                  75                  80 caa gtc ttc tca gat cca caa gta cta aac ttc ttc gcg aat cca aca    288
Gln Val Phe Ser Asp Pro Gln Val Leu Asn Phe Phe Ala Asn Pro Thr
                 85                  90                  95 atc acc gtc gag aag aaa cgt caa gtc atc gac gac ata gtg aaa tcg    336
Ile Thr Val Glu Lys Lys Arg Gln Val Ile Asp Asp Ile Val Lys Ser
            100                 105                 110 tcg tct ctt caa tct cac aca tct aac ttc ctc aac gtc ctc gtc gac    384
Ser Ser Leu Gln Ser His Thr Ser Asn Phe Leu Asn Val Leu Val Asp
        115                 120                 125 gcg aat cgg atc aat atc gtg acg gag atc gtt aag gag ttt gag ttg    432
Ala Asn Arg Ile Asn Ile Val Thr Glu Ile Val Lys Glu Phe Glu Leu
    130                 135                 140 gtt tac aat aag cta acg gat aca caa ttg gcg gag gtt agg tcg gtg    480
Val Tyr Asn Lys Leu Thr Asp Thr Gln Leu Ala Glu Val Arg Ser Val
145                 150                 155                 160 gtg aaa ttg gaa gcg ccg caa tta gct cag att gcg aaa cag gtt cag    528
Val Lys Leu Glu Ala Pro Gln Leu Ala Gln Ile Ala Lys Gln Val Gln
                165                 170                 175 aag tta acc gga gct aag aat gtt cgg gtt aag acg gtt att gat gcg    576
Lys Leu Thr Gly Ala Lys Asn Val Arg Val Lys Thr Val Ile Asp Ala
            180                 185                 190 agt ctt gtg gct ggt ttt acg att cgg tat ggt gaa tcc ggt tcg aag    624
Ser Leu Val Ala Gly Phe Thr Ile Arg Tyr Gly Glu Ser Gly Ser Lys
        195                 200                 205 ctt att gat atg agt gtg aag aaa cag ctt gaa gat att gct tct cag    672
Leu Ile Asp Met Ser Val Lys Lys Gln Leu Glu Asp Ile Ala Ser Gln
    210                 215                 220 ctt gaa ctt ggt gag att caa tta gct act tga                        705
Leu Glu Leu Gly Glu Ile Gln Leu Ala Thr
225                 230                 235

<210> SEQ ID NO 22
<211> LENGTH: 234
<212> TYPE: PRT
```

<213> ORGANISM: Arabidopsis thaliana

<400> SEQUENCE: 22

```
Met Ala Ser Leu Gln Gln Thr Leu Phe Ser Leu Gln Ser Lys Leu Pro
1               5                   10                  15

Pro Ser Ser Phe Gln Ile Ala Arg Ser Leu Pro Leu Arg Lys Thr Phe
            20                  25                  30

Pro Ile Arg Ile Asn Asn Gly Gly Asn Ala Ala Gly Ala Arg Met Ser
        35                  40                  45

Ala Thr Ala Ala Ser Ser Tyr Ala Met Ala Leu Ala Asp Val Ala Lys
    50                  55                  60

Arg Asn Asp Thr Met Glu Leu Thr Val Thr Asp Ile Glu Lys Leu Glu
65              70                  75                  80

Gln Val Phe Ser Asp Pro Gln Val Leu Asn Phe Ala Asn Pro Thr
                85                  90                  95

Ile Thr Val Glu Lys Lys Arg Gln Val Ile Asp Ile Val Lys Ser
            100                 105                 110

Ser Ser Leu Gln Ser His Thr Ser Asn Phe Leu Asn Val Leu Val Asp
        115                 120                 125

Ala Asn Arg Ile Asn Ile Val Thr Glu Ile Val Lys Glu Phe Glu Leu
    130                 135                 140

Val Tyr Asn Lys Leu Thr Asp Thr Gln Leu Ala Glu Val Arg Ser Val
145             150                 155                 160

Val Lys Leu Glu Ala Pro Gln Leu Ala Gln Ile Ala Lys Gln Val Gln
                165                 170                 175

Lys Leu Thr Gly Ala Lys Asn Val Arg Val Lys Thr Val Ile Asp Ala
            180                 185                 190

Ser Leu Val Ala Gly Phe Thr Ile Arg Tyr Gly Glu Ser Gly Ser Lys
        195                 200                 205

Leu Ile Asp Met Ser Val Lys Lys Gln Leu Glu Asp Ile Ala Ser Gln
    210                 215                 220

Leu Glu Leu Gly Glu Ile Gln Leu Ala Thr
225                 230
```

<210> SEQ ID NO 23
<211> LENGTH: 1011
<212> TYPE: DNA
<213> ORGANISM: Arabidopsis thaliana

<400> SEQUENCE: 23

```
aaccacaaat ctctctttct ctcaaactct ctcaacaaca acaatggcgt ctcttcaaca      60
aactctattc tctcttcaat ccaaactccc accatcctcc ttccaaatcg ccagatctct     120
cccactccga aaaccttcc caatccgaat caacaacggt ggaaacgccg ccggagcaag      180
aatgtcagcc accgcagcat caagctacgc gatggcatta gcagacgtcg cgaaaagaaa     240
cgacacaatg gaattaacag tcacagacat cgagaagctc gaacaagtct tctcagatcc     300
acaagtacta aacttcttcg cgaatccaac aatcaccgtc gagaagaaac gtcaagtcat     360
cgacgacata gtgaaatcgt cgtctcttca atctcacaca tctaacttcc tcaacgtcct     420
cgtcgacgcg aatcggatca atatcgtgac ggagatcgtt aaggagtttg agttggttta     480
caataagcta acggatacac aattggcgga ggttaggtcg gtggtgaaat ggaagcgcc     540 gcaattagct cagattgcga aacaggttca gaagttaacc ggagctaaga atgttcgggt     600
taagacggtt attgatgcga gtcttgtggc tggttttacg attcggtatg gtgaatccgg     660
```

-continued

```
ttcgaagctt attgatatga gtgtgaagaa acagcttgaa gatattgctt ctcagcttga      720
acttggtgag attcaattag ctacttgaga tttgggaaaa attgtataag agaaaaattt      780
gagaatcttt tttttttgtg caagtttaat tttttttctc ctcatcttct ttctctatta      840
atcaatcata taatatacag tactgatgat ataataatga ttctgagttt attatctttg      900
taattgttaa atttagtgaa ttcgaaaacg aattcgaata gtatgtttgc ggattatgcg      960
ttttggggaa tggttttact gttaaattgc ggttaatctc ggttgaatag a             1011
```

```
<210> SEQ ID NO 24
<211> LENGTH: 21
<212> TYPE: DNA
<213> ORGANISM: Arabidopsis thaliana
<220> FEATURE:
<221> NAME/KEY: 5'UTR
<222> LOCATION: (1)..(21)

<400> SEQUENCE: 24
caaactctct caacaacaac a                                               21

<210> SEQ ID NO 25
<211> LENGTH: 192
<212> TYPE: DNA
<213> ORGANISM: Arabidopsis thaliana
<220> FEATURE:
<221> NAME/KEY: 3'UTR
<222> LOCATION: (1)..(192)

<400> SEQUENCE: 25
gatttgggaa aaattgtata agagaaaaat ttgagaatct ttttttttg tgcaagttta       60 atttttttc tcctcatctt ctttctctat taatcaatca tataatatac agtactgatg      120
atataataat gattctgagt ttattatctt tgtaattgtt aaatttagtg aattcgaaaa     180
cgaattcgaa ta                                                         192

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26
gcggacatct acatttttga                                                  20
```

HERBICIDE TARGET GENES AND METHODS

This application claims the benefit of U.S. Provisional Application No. 60/229,353, filed Mar. 5, 1999. This application also claims the benefit of U.S. Provisional Application No. 60/228,817, filed Jun. 8, 1999. This application also claims the benefit of these priority documents are hereby expressly incorporated by reference in their entirety into the instant disclosure.

FIELD OF THE INVENTION

The invention relates to genes isolated from *Arabidopsis thaliana* that encode proteins essential for plant growth and development. The invention also includes the methods of using these proteins as herbicide targets, based on the essentiality of these genes for normal growth and development. The invention is also useful as a screening assay to identify inhibitors that are potential herbicides. The invention may also be applied to the development of herbicide tolerant plants, plant tissues, plant seeds, and plant cells.

BACKGROUND OF THE INVENTION

The use of herbicides to control undesirable vegetation such as weeds in crop fields has become almost a universal practice. The herbicide market exceeds 15 billion dollars annually. Despite this extensive use, weed control remains a significant and costly problem for farmers.

Effective use of herbicides requires sound management. For instance, the time and method of application and stage of weed plant development are critical to getting good weed control with herbicides. Since various weed species are resistant to herbicides, the production of effective new herbicides becomes increasingly important. Novel herbicides can now be discovered using high-throughput screens that implement recombinant DNA technology. Metabolic enzymes found to be essential to plant growth and development can be recombinantly produced through standard molecular biological techniques and utilized as herbicide targets in screens for novel inhibitors of the enzyme activity. The novel inhibitors discovered through such screens may then be used as herbicides to control undesirable vegetation.

Herbicides that exhibit greater potency, broader weed spectrum, and more rapid degradation in soil can also, unfortunately, have greater crop phytotoxicity. One solution applied to this problem has been to develop crops that are resistant or tolerant to herbicides. Crop hybrids or varieties tolerant to the herbicides allow for the use of the herbicides to kill weeds without attendant risk of damage to the crop. Development of tolerance can allow application of a herbicide to a crop where its use was previously precluded or limited (e.g to pre-emergence use) due to sensitivity of the crop to the herbicide. For example, U.S. Pat. No. 4,761,373 to Anderson et al. is directed to plants resistant to various imidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants expressing a mutant acetolactate synthase that renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase (ACCase).

Notwithstanding the above-described advancements, there remains a persistent and ongoing problem with unwanted or detrimental vegetation growth (e.g. weeds). Furthermore, as the population continues to grow, there will be increasing food shortages. Therefore, there exists a long felt, yet unfulfilled need, to find new, effective, and economic herbicides.

SUMMARY OF THE INVENTION

It is an object of the invention to provide an effective and beneficial method to identify novel herbicides. A feature of the invention is the identification of a gene in *A. thaliana*, herein referred to as the 8388 gene, which shows sequence similarity to DEAD box RNA helicase (Luking et al. (1998) Critical Reviews in Biochemistry and Molecular Biology, 33(4): 259–296). A feature of the invention is the identification of a gene in *A. thaliana*, herein referred to as the 18048 gene, which shows sequence similarity to ADP-ribosylation factor (Art) genes (Regad et al. (1993) FEBS Lett. 25: 133–136; Bar-Peled et al. (1995) The Plant Cell, 7: 667–676). A feature of the invention is the identification of a gene in *A. thaliana*, herein referred to as the 16713 gene, which shows sequence similarity to acetoacetyl coA thiolases (Vollack and Bach (1996) Plant Physiol. 111: 1097–1107; Hiser et al. (1994) J. Biol. Chem. 269: 31383–31389; Fukao et al. (1990) J. Clin. Invest. 86: 2086–2092; Fukao et al. (1989) J. Biochem. 106: 197–204; Wilson et al. (1994) Nature 368: 32–38). A feature of the invention is the identification of a gene in Arabidopsis, herein referred to as the 4144 gene, which encodes a protein with sequence similarity to chloroplast ATP synthase delta chain (Hermans et al. (1988) Plant Mol. Biol. 10: 323–330; Hoesche and Berzborn (1992) Biochimica et Biophysica Acta, 1171: 201–204; Hoesche and Berzbom (1993) Biochimica et Biophysica Acta, 1142: 293–305; Napier et al. (1992) Plant Mol. Biol. 20: 549–554). Another feature of the invention is the discovery that the 8388, 18048, 16713, and 4144 genes are essential for normal growth and development. An advantage of the present invention is that the newly discovered essential genes provide the basis for identity of a novel herbicidal mode of action which enables one skilled in the art to easily and rapidly discover novel inhibitors of gene function useful as herbicides.

One object of the present invention is to provide essential genes in plants for assay development for inhibitory compounds with herbicidal activity. Genetic results show that when any one of the 8388, 18048, 16713, or 4144 genes is mutated in *Arabidopsis thaliana*, the resulting phenotype is lethal in the homozygous state. This suggests a critical role for the gene products encoded by the 8388, 18048, 16713, and 4144 genes.

Using T-DNA insertion mutagenesis, the inventors of the present invention have demonstrated that the activity of any one of the 8388, 18048, 16713, or 4144 gene products is essential for *A. thaliana* growth. This implies that chemicals, which inhibit the function of the 8388, 18048, 16713, or 4144-encoded protein in plants, are likely to have detrimental effects on plants and are potentially good herbicide candidates. The present invention therefore provides methods of using a purified protein encoded by the 8388, 18048, 16713, or 4144 gene sequence described below to identify inhibitors thereof, which can then be used as herbicides to suppress the growth of undesirable vegetation, e.g. in fields where crops are grown, particularly agronomically important crops such as maize and other cereal crops such as wheat, oats, rye, sorghum, rice, barley, millet, turf and forage grasses, and the like, as well as cotton, sugar cane, sugar beet, oilseed rape, and soybeans.

The present invention discloses novel nucleotide sequences derived from A. thaliana, designated the 8388, 18048, 16713, or 4144 genes. The nucleotide sequences of the coding regions for the cDNA clones are set forth in SEQ ID NO:1, SEQ ID NO:5, SEQ ID NO:7, and SEQ ID NO:21, respectively, and the corresponding amino acid sequences of the 8388, 18048, 16713, or 4144-encoded protein are set forth in SEQ ID NO:2, SEQ ID NO:6, SEQ ID NO:8, and SEQ ID NO:22, respectively. The present invention also includes nucleotide sequences substantially similar to those set forth in SEQ ID NO:1, SEQ ID NO:5, SEQ ID NO:7, and SEQ ID NO:21, respectively. The present invention also encompasses plant proteins whose amino acid sequence are substantially similar to the amino acid sequences set forth in SEQ ID NO:2, SEQ ID NO:6, SEQ ID NO:8, and SEQ ID NO:22, respectively. The present invention also includes methods of using the 8388, 18048, 16713, or 4144 gene products as herbicide targets, based on the essentiality of these genes for normal growth and development. Furthermore, the invention can be used in a screening assay to identify inhibitors of 8388, 18048, 16713, or 4144 gene function that are potential herbicides.

In a preferred embodiment, the present invention relates to a method for identifying chemicals having the ability to inhibit 8388, 18048, 16713, or 4144 activity in plants preferably comprising the steps of: a) obtaining transgenic plants, plant tissue, plant seeds or plant cells, preferably stably transformed, comprising a non-native nucleotide sequence encoding an enzyme having 8388, 18048, 16713, or 4144 activity and capable of overexpressing an enzymatically active 8388, 18048, 16713, or 4144 gene product (either full length or truncated but still active); b) applying a chemical to the transgenic plants, plant cells, tissues or parts and to the isogenic non-transformed plants, plant cells, tissues or parts; c) determining the growth or viability of the transgenic and non-transformed plants, plant cells, tissues after application of the chemical; d) comparing the growth or viability of the transgenic and non-transformed plants, plant cells, tissues after application of the chemical; and e) selecting chemicals that suppress the viability or growth of the non-transgenic plants, plant cells, tissues or parts, without significantly suppressing the growth of the viability or growth of the isogenic transgenic plants, plant cells, tissues or parts. In a preferred embodiment, the enzyme having 8388, 18048, 16713, or 4144 activity is encoded by a nucleotide sequence derived from a plant, preferably Arabidopsis thaliana, desirably identical or substantially similar to the nucleotide sequence set forth in SEQ ID NO:1, SEQ ID NO:5, SEQ ID NO:7, and SEQ ID NO:21, respectively. In another embodiment, the enzyme having 8388, 18048, 16713, or 4144 activity is encoded by a nucleotide sequence capable of encoding the amino acid sequence of SEQ ID NO:2, SEQ ID NO:6, SEQ ID NO:8, and SEQ ID NO:22, respectively. In yet another embodiment, the enzyme having 8388, 18048, 16713, or 4144 activity has an amino acid sequence identical or substantially similar to the amino acid sequence set forth in SEQ ID NO:2, SEQ ID NO:6, SEQ ID NO:8, and SEQ ID NO:22, respectively.

The present invention further embodies plants, plant tissues, plant seeds, and plant cells that have modified 8388, 18048, 16713, or 4144 activity and that are therefore tolerant to inhibition by a herbicide at levels normally inhibitory to naturally occurring 8388, 18048, 16713, or 4144-encoded activity. Herbicide tolerant plants encompassed by the invention include those that would otherwise be potential targets for 8388, 18048, 16713, or 4144-inhibiting herbicides, particularly the agronomically important crops mentioned above. According to this embodiment, plants, plant tissue, plant seeds, or plant cells are transformed, preferably stably transformed, with a recombinant DNA molecule comprising a suitable promoter functional in plants operatively linked to a nucleotide sequence that encodes a modified 8388, 18048, 16713, or 4144 gene that is tolerant to inhibition by a herbicide at a concentration that would normally inhibit the activity of wild-type, unmodified 8388, 18048, 16713, or 4144 gene product. Modified 8388, 18048, 16713, or 4144 activity may also be conferred upon a plant by increasing expression of wild-type herbicide-sensitive 8388, 18048, 16713, or 4144 protein by providing multiple copies of wild-type 8388, 18048, 16713, or 4144 genes to the plant or by overexpression of wild-type 8388, 18048, 16713, or 4144 genes under control of a stronger-than-wild-type promoter. The transgenic plants, plant tissue, plant seeds, or plant cells thus created are then selected using conventional techniques, whereby herbicide tolerant lines are isolated, characterized, and developed. Alternately, random or site-specific mutagenesis may be used to generate herbicide tolerant lines.

Therefore, the present invention provides a plant, plant cell, plant seed, or plant tissue transformed with a DNA molecule comprising a nucleotide sequence isolated from a plant that encodes an enzyme having 8388, 18048, 16713, or 4144 activity, wherein the DNA expresses the 8388, 18048, 16713, or 4144 activity and wherein the DNA molecule confers upon the plant, plant cell, plant seed, or plant tissue tolerance to a herbicide in amounts that normally inhibits naturally occurring 8388, 18048, 16713, or 4144 activity. According to one example of this embodiment, the enzyme having 8388, 18048, 16713, or 4144 activity is encoded by a nucleotide sequence identical or substantially similar to the nucleotide sequence set forth in SEQ ID NO:1, SEQ ID NO:5, SEQ ID NO:7, and SEQ ID NO:21, respectively, or has an amino acid sequence identical or substantially similar to the amino acid sequence set forth in SEQ ID NO:2, SEQ ID NO:6, SEQ ID NO:8, and SEQ ID NO:22, respectively.

The invention also provides a method for suppressing the growth of a plant comprising the step of applying to the plant a chemical that inhibits the naturally occurring 8388, 18048, 16713, or 4144 activity in the plant. In a related aspect, the present invention is directed to a method for selectively suppressing the growth of undesired vegetation in a field containing a crop of planted crop seeds or plants, comprising the steps of: (a) optionally planting herbicide tolerant crops or crop seeds, which are plants or plant seeds that are tolerant to a herbicide that inhibits the naturally occurring 8388, 18048, 16713, or 4144 activity; and (b) applying to the herbicide tolerant crops or crop seeds and the undesired vegetation in the field a herbicide in amounts that inhibit naturally occurring 8388, 18048, 16713, or 4144 activity, wherein the herbicide suppresses the growth of the weeds without significantly suppressing the growth of the crops.

The invention thus provides an isolated DNA molecule comprising a nucleotide sequence substantially similar to SEQ ID NO:1, SEQ ID NO:5, SEQ ID NO:7, or SEQ ID NO:21, respectively. In a preferred embodiment, the nucleotide sequence encodes an amino acid sequence substantially similar to SEQ ID NO:2, SEQ ID NO:6, SEQ ID NO:8, or SEQ ID NO:22, respectively. In another preferred embodiment, the nucleotide sequence is SEQ ID NO:1, SEQ ID NO:5, SEQ ID NO:7, or SEQ ID NO:21, respectively. In yet another preferred embodiment, the nucleotide sequence encodes the amino acid sequence of SEQ ID NO:2, SEQ ID NO:6, SEQ ID NO:8, or SEQ ID NO:22, respectively. Preferably, the nucleotide sequence is a plant nucleotide sequence, which preferably encodes a polypeptide having 8388, 18048, 16713, or 4144 activity, respectively.

The invention further provides a polypeptide comprising an amino acid sequence encoded by a nucleotide sequence substantially similar to SEQ ID NO:1, SEQ ID NO:5, SEQ ID NO:7, or SEQ ID NO:21, respectively. Preferably, the amino acid sequence is encoded by SEQ ID NO:1, SEQ ID NO:5, SEQ ID NO:7, or SEQ ID NO:21, respectively. Preferably, the polypeptide comprises an amino acid sequence substantially similar to SEQ ID NO:2, SEQ ID NO:6, SEQ ID NO:8, or SEQ ID NO:22, respectively. Preferably the amino acid sequence is SEQ ID NO:2, SEQ ID NO:6, SEQ ID NO:8, or SEQ ID NO:22, respectively. The amino acid sequence preferably has 8388, 18048, 16713, or 4144 activity, respectively. In another preferred embodiment, the amino acid sequence comprises at least 20 consecutive amino acid residues of the amino acid sequence encoded by SEQ ID NO:1, SEQ ID NO:5, SEQ ID NO:7, or SEQ ID NO:21, respectively. Or, alternatively, the amino acid sequence comprises at least 20 consecutive amino acid residues of the amino acid sequence of SEQ ID NO:2, SEQ ID NO:6, SEQ ID NO:8, or SEQ ID NO:22, respectively. The invention further provides an expression cassette comprising a promoter operatively linked to a DNA molecule according to the present invention, a recombinant vector comprising an expression cassette according to the present invention, wherein said vector is preferably capable of being stably transformed into a host cell, a host cell comprising a DNA molecule according to the present invention, wherein said DNA molecule is preferably expressible in the cell. The host cell is preferably selected from the group consisting of an insect cell, a yeast cell, a prokaryotic cell and a plant cell. The invention further provides a plant or seed comprising a plant cell of the present invention, wherein the plant or seed is preferably tolerant to an inhibitor of 8388, 18048, 16713, or 4144 activity, respectively.

The invention further provides a process for making nucleotides sequences encoding gene products having altered 8388, 18048, 16713, or 4144 activity, respectively, comprising: a) shuffling an unmodified nucleotide sequence of the present invention, b) expressing the resulting shuffled nucleotide sequences, and c) selecting for altered 8388, 18048, 16713, or 4144 activity, respectively, as compared to the 8388, 18048, 16713, or 4144 activity, respectively, of the gene product of said unmodified nucleotide sequence.

In a preferred embodiment, the unmodified nucleotide sequence is identical or substantially similar to SEQ ID NO:1, SEQ ID NO:5, SEQ ID NO:7, or SEQ ID NO:21, respectively, or a homolog thereof. The present invention further provides a DNA molecule comprising a shuffled nucleotide sequence obtainable by the process described above, a DNA molecule comprising a shuffled nucleotide sequence produced by the process described above. Preferably, a shuffled nucleotide sequence obtained by the process described above has enhanced tolerance to an inhibitor of 8388, 18048, 16713, or 4144 activity, respectively. The invention further provides an expression cassette comprising a promoter operatively linked to a DNA molecule comprising a shuffled nucleotide sequence a recombinant vector comprising such an expression cassette, wherein said vector is preferably capable of being stably transformed into a host cell, a host cell comprising such an expression cassette, wherein said nucleotide sequence is preferably expressible in said cell. A preferred host cell is selected from the group consisting of an insect cell, a yeast cell, a prokaryotic cell and a plant cell. The invention further provides a plant or seed comprising such plant cell, wherein the plant is preferably tolerant to an inhibitor of 8388, 18048, 16713, or 4144 activity, respectively.

The invention further provides a method for selecting compounds that interact with the protein encoded by SEQ ID NO:1, SEQ ID NO:5, SEQ ID NO:7, or SEQ ID NO:21, respectively, comprising: a) expressing a DNA molecule comprising SEQ ID NO:1, SEQ ID NO:5, SEQ ID NO:7. or SEQ ID NO:21, respectively, or a sequence substantially similar to SEQ ID NO:1, SEQ ID NO:5, SEQ ID NO:7, or SEQ ID NO:21, respectively, or a homolog thereof, to generate the corresponding protein, b) testing a compound suspected of having the ability to interact with the protein expressed in step (a), and c) selecting compounds that interact with the protein in step (b).

The invention further provides a process of identifying an inhibitor of 8388, 18048, 16713, or 4144 activity, respectively, comprising: a) introducing a DNA molecule comprising a nucleotide sequence of SEQ ID NO:1, SEQ ID NO:5, SEQ ID NO:7, or SEQ ID NO:21, respectively, and having 8388, 18048, 16713, or 4144 activity, respectively, or nucleotide sequences substantially similar thereto, or a homolog thereof, into a plant cell, such that said sequence is functionally expressible at levels that are higher than wild-type expression levels, b) combining said plant cell with a compound to be tested for the ability to inhibit the 8388, 18048, 16713, or 4144 activity, respectively, under conditions conducive to such inhibition, c) measuring plant cell growth under the conditions of step (b), d) comparing the growth of said plant cell with the growth of a plant cell having unaltered 8388, 18048, 16713, or 4144 activity, respectively, under identical conditions, and e) selecting said compound that inhibits plant cell growth in step (d).

The invention further comprises a compound having herbicidal activity identifiable according to the process described immediately above.

The invention further comprises:
A process of identifying compounds having herbicidal activity comprising:
  a) combining a protein of the present invention and a compound to be tested for the ability to interact with said protein, under conditions conducive to interaction, b) selecting a compound identified in step (a) that is capable of interacting with said protein, c) applying identified compound in step (b) to a plant to test for herbicidal activity, and d) selecting compounds having herbicidal activity.

The invention further comprises a compound having herbicidal activity identifiable according to the process described immediately above.

The invention further comprises:
A method for suppressing the growth of a plant comprising, applying to said plant a compound that inhibits the activity of a polypeptide of the present invention in an amount sufficient to suppress the growth of said plant.

The invention further comprises:
A method for recombinantly expressing a protein having 8388, 18048, 16713, or 4144 activity comprising introducing a nucleotide sequence encoding a protein having one of the above activities into a host cell and expressing the nucleotide sequence in the host cell. A preferred host cell is selected from the group consisting of an insect cell, a yeast cell, a prokaryotic cell and a plant cell. A preferred prokaryotic cell is a bacterial cell, e.g. *E. coli*.

Other objects and advantages of the present invention will become apparent to those skilled in the art from a study of the following description of the invention and non-limiting examples.

DEFINITIONS

For clarity, certain terms used in the specification are defined and presented as follows:

Cofactor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

DNA shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme activity: means herein the ability of an enzyme to catalyze the conversion of a substrate into a product. A substrate for the enzyme comprises the natural substrate of the enzyme but also comprises analogues of the natural substrate which can also be converted by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Herbicide: a chemical substance used to kill or suppress the growth of plants, plant cells, plant seeds, or plant tissues.

Heterologous DNA Sequence: a DNA sequence not naturally associated with a host cell into which it is introduced, including non-naturally occurring multiple copies of a naturally occurring DNA sequence; and genetic constructs wherein an otherwise homologous DNA sequence is operatively linked to a non-native sequence.

Homologous DNA Sequence: a DNA sequence naturally associated with a host cell into which it is introduced.

Inhibitor: a chemical substance that causes abnormal growth, e.g., by inactivating the enzymatic activity of a protein such as a biosynthetic enzyme, receptor, signal transduction protein, structural gene product, or transport protein that is essential to the growth or survival of the plant. In the context of the instant invention, an inhibitor is a chemical substance that alters the enzymatic activity encoded by a nucleotide sequence of the present invention. More generally, an inhibitor causes abnormal growth of a host cell by interacting with the gene product encoded by the nucleotide sequence of the present invention.

Isogenic: plants which are genetically identical, except that they may differ by the presence or absence of a heterologous DNA sequence.

Isolated: in the context of the present invention, an isolated DNA molecule or an isolated enzyme is a DNA molecule or enzyme that, by the hand of man, exists apart from its native environment and is therefore not a product of nature. An isolated DNA molecule or enzyme may exist in a purified form or may exist in a non-native environment such as, for example, in a transgenic host cell.

Mature protein: protein which is normally targeted to a cellular organelle, such as a chloroplast, and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Pre-protein: protein which is normally targeted to a cellular organelle, such as a chloroplast, and still comprising its transit peptide.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

Significantly less: means that the amount of a product of an enzymatic reaction is reduced by more than the margin of error inherent in the measurement technique, preferably a decrease by about 2-fold or greater of the activity of the wild-type enzyme in the absence of the inhibitor, more preferably an decrease by about 5-fold or greater, and most preferably an decrease by about 10-fold or greater.

Substantially similar: with respect to the 8388 gene, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln/index.html). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "8388 gene" refers to a DNA molecule comprising SEQ ID NO:1 or comprising a nucleotide sequence substantially similar to SEQ ID NO:1. Homologs of the 8388 gene include nucleotide sequences that encode an amino acid sequence that is at least 25% identical to SEQ ID NO:2 as measured, using the parameters described below, wherein the amino acid sequence encoded by the homolog has the biological activity of the 8388 protein.

With respect to the 8388 protein, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%, using default BLAST analysis parameters BLAST 2.0.7. As used herein the term "8388 protein" refers to an amino acid sequence encoded by a DNA molecule comprising a nucleotide sequence substantially similar to SEQ ID NO:1. Homologs of the 8388 protein are amino acid sequences that are at (again here) least 25% identical to SEQ ID NO:2, as measured using the parameters described above, wherein the amino acid sequence encoded by the homolog has the biological activity ofthe 8388 protein.

With respect to the 18048 gene, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln/index.html). The local S program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "18048 gene" refers to a DNA molecule comprising SEQ ID NO:5 or comprising a nucleotide sequence substantially similar to SEQ ID NO:5. Homologs of the 18048 gene include nucleotide sequences that encode an amino acid sequence that is at least 30% identical to SEQ ID NO:6 as measured, using the parameters described below, wherein the amino acid sequence encoded by the homolog has the biological activity of the 18048 protein.

With respect to the 18048 protein, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%, using default BLAST analysis parameters BLAST 2.0.7. As used herein the term "18048 protein" refers to an amino acid sequence encoded by a DNA molecule comprising a nucleotide sequence substantially similar to SEQ ID NO:5. Homologs of the 18048 protein are amino acid sequences that are at least 30% identical to SEQ ID NO:6, as measured using the parameters described above, wherein the amino acid sequence encoded by the homolog has the biological activity of the 18048 protein.

With respect to the 16713 gene, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 90%, more desirably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln/index.html). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "16713 gene" refers to a DNA molecule comprising SEQ ID NO:7 or comprising a nucleotide sequence substantially similar to SEQ ID NO:7. Homologs of the 16713 gene include nucleotide sequences that encode an amino acid sequence that is at least 45% identical, preferably at least 55%, more preferably at least 65%, still more preferably at least 75%, yet still more preferably at least 85% identical to SEQ ID NO:8 as measured, using the parameters described below, wherein the amino acid sequence encoded by the homolog has the biological activity of the 16713 protein.

With respect to the 16713 protein, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 93%, still more preferably at least 95%, yet still more preferably at least 99%, using default BLAST analysis parameters BLAST 2.0.7. As used herein the term "16713 protein" refers to an amino acid sequence encoded by a DNA molecule comprising a nucleotide sequence substantially similar to SEQ ID NO:7. Homologs of the 16713 protein are amino acid sequences that are at least 45% identical, preferably at least 55%, more preferably at least 65%, still more preferably at least 75%, yet still more preferably at least 85% identical to SEQ ID NO:8, as measured using the parameters described above, wherein the amino acid sequence encoded by the homolog has the biological activity of the 16713 protein.

With respect to the 4144 gene, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln/index.html). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "4144 gene" refers to a DNA molecule comprising SEQ ID NO:21 or comprising a nucleotide sequence substantially similar to SEQ ID NO:21. Homlologs of the 4144 gene include nucleotide sequences that encode an amino acid sequence that is at least 30% identical to SEQ ID NO:22 as measured using the parameters described below, wherein the amino acid sequence encoded by the homolog has the biological activity of the 4144 protein.

With respect to the 4144 protein, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%, using default BLAST analysis parameters. As used herein the term "4144 protein" refers to an amino acid sequence encoded by a DNA molecule comprising a nucleotide sequence substantially similar to SEQ ID NO:21. Homologs of the 4144 protein are amino acid sequences that are at least 30% identical to SEQ ID NO:22, as measured using the parameters described above, wherein the amino acid sequence encoded by the homolog has the biological activity of the 4144 protein.

One skilled in the art is also familiar with other analysis tools, such as GAP analysis, to determine the percentage of identity between the "substantially similar" and the reference nucleotide sequence, or protein or amino acid sequence. In the present invention, "substantially similar" is therefore also determined using default GAP analysis parameters with the University of Wisconsin GCG, SEQWEB application of GAP, based on the algorithm of Needleman and Wunsch (Needleman and Wunsch (1970) J Mol. Biol. 48: 443–453).

Thus, in the context of the "8388 gene" and using GAP analysis as described above, "substantially similar" refers to nucleotide sequences that encode a protein having at least 37% identity, more preferably at least 50% identity, still more preferably at least 65% identity, still more preferably at least 75% identity, still more preferably at least 85% identity, still more preferably at least 95% identity, yet still more preferably at least 99% identity to SEQ ID NO:2. Further, using GAP analysis as described above, "homologs of the 8388 gene" include nucleotide sequences that encode an amino acid sequence that has at least 29% identity to SEQ ID NO:2, more preferably at least 35% identity, still more preferably at least 45% identity, still more preferably at least 55% identity, yet still more preferably at least 65% identity, still more preferably at least 75% identity, yet still more preferably at least 85% identity to SEQ ID NO:2, wherein the amino acid sequence encoded by the homolog has the biological activity of the 8388 protein.

When using GAP analysis as described above with respect to a protein or an amino acid sequence and in the context of the "8388 gene", the percentage of identity between the "substantially similar" protein or amino acid sequence and the reference protein or amino acid sequence (in this case SEQ ID NO:2) is at least 37%, more preferably at least 50%, still more preferably at least 65%, still more preferably at least 75%, still more preferably at least 85%, still more preferably at least 95%, yet still more preferably at least 99%. "Homologs of the 8388 protein" include amino acid sequences that are at least 29% identical to SEQ ID NO:2, more preferably at least 35% identical, still more preferably at least 45% identical, still more preferably at least 55% identical, yet still more preferably at least 65% identical, still more preferably at least 75% identical, yet still more preferably at least 85% identical to SEQ ID NO:2, wherein homologs of the 8388 protein have the biological activity of the 8388 protein.

Thus, in the context of the "18048 gene" and using GAP analysis as described above, "substantially similar" refers to nucleotide sequences that encode a protein having at least 64% identity, more preferably at least 70% identity, still more preferably at least 75% identity, still more preferably at least 85% identity, still more preferably at least 95% identity, yet still more preferably at least 99% identity to SEQ ID NO:6. Further, using GAP analysis as described above, "homologs of the 18048 gene" include nucleotide sequences that encode an amino acid sequence that has at least 45% identity to SEQ ID NO:6, more preferably at least 50% identity, still more preferably at least 55% identity, still more preferably at least 60% identity, yet still more preferably at least 65% identity, still more preferably at least 75% identity, yet still more preferably at least 85% identity to SEQ ID NO:6, wherein the amino acid sequence encoded by the homolog has the biological activity of the 18048 protein.

When using GAP analysis as described above with respect to a protein or an amino acid sequence and in the context of the "18048 gene", the percentage of identity between the "substantially similar" protein or amino acid sequence and the reference protein or amino acid sequence (in this case SEQ ID NO:6) is at least 64%, more preferably at least 70%, still more preferably at least 75%, still more preferably at least 85%, still more preferably at least 95%, yet still more preferably at least 99%. "Homologs of the 18048 protein" include amino acid sequences that are at least 45% identical to SEQ ID NO:6, more preferably at least 50% identical, still more preferably at least 55% identical, still more preferably at least 60% identical, yet still more preferably at least 65% identical, still more preferably at least 75% identical, yet still more preferably at least 85% identical to SEQ ID NO:6, wherein homologs of the 18048 protein have the biological activity of the 18048 protein.

Thus, in the context of the "16713 gene" and using GAP analysis as described above, "substantially similar" refers to nucleotide sequences that encode a protein having at least 93% identity, more preferably at least 95% identity, still more preferably at least 99% identity to SEQ ID NO:8. Further, using GAP analysis as described above, "homologs of the 16713 gene" include nucleotide sequences that encode an amino acid sequence that has at least 45% identity to SEQ ID NO:8, more preferably at least 50% identity, still more preferably at least 55% identity, still more preferably at least 60% identity, yet still more preferably at least 70% identity, still more preferably at least 85% identity, yet still more preferably at least 90% identity to SEQ ID NO:8, wherein the amino acid sequence encoded by the homolog has the biological activity of the 16713 protein.

When using GAP analysis as described above with respect to a protein or an amino acid sequence and in the context of the "16713 gene", the percentage of identity between the "substantially similar" protein or amino acid sequence and the reference protein or amino acid sequence (in this case SEQ ID NO:8) is at least 93%, more preferably at least 95%, still more preferably at least 99%. "Homologs of the 16713 protein" include amino acid sequences that are at least 45% identical to SEQ ID NO:8, more preferably at least 50% identical, still more preferably at least 55% identical, still more preferably at least 60% identical, yet still more preferably at least 70% identical, still more preferably at least 85% identical, yet still more preferably at least 95% identical to SEQ ID NO:8, wherein honiologs of the 16713 protein have the biological activity of the 16713 protein.

Thus, in the context of the "4144 gene" and using GAP analysis as described above, "substantially similar" refers to nucleotide sequences that encode a protein having at least 89% identity, more preferably at least 90% identity, still more preferably at least 95% identity, yet still more preferably at least 99% identity to SEQ ID NO:22. Further, using GAP analysis as described above, "homologs of the 4144 gene" include nucleotide sequences that encode an amino acid sequence that has at least 45% identity to SEQ ID NO:22, more preferably at least 50% identity, still more preferably at least 55% identity, still more preferably at least 60% identity, yet still more preferably at least 65% identity, still more preferably at least 75% identity, yet still more preferably at least 85% identity to SEQ ID NO:22, wherein the amino acid sequence encoded by the homolog has the biological activity of the 4144 protein.

When using GAP analysis as described above with respect to a protein or an amino acid sequence and in the context of the "4144 gene", the percentage of identity between the "substantially similar" protein or amino acid sequence and the reference protein or amino acid sequence (in this case SEQ ID NO:22) is at least 89%, more preferably at least 90%, still more preferably at least 95%, yet still more preferably at least 99%. "Homologs of the 4144 protein" include amino acid sequences that are at least 45% identical to SEQ ID NO:22, more preferably at least 50% identical, still more preferably at least 55% identical, still more preferably at least 60% identical, yet still more preferably at least 65% identical, still more preferably at least 75% identical, yet still more preferably at least 85% identical to SEQ ID NO:8, wherein homologs of the 4144 protein have the biological activity of the 4144 protein.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Tolerance: the ability to continue essentially normal growth or function when exposed to an inhibitor or herbicide in an amount sufficient to suppress the normal growth or function of native, unmodified plants.

Transformation: a process for introducing heterologous DNA into a cell, tissue, or plant. Transformed cells, tissues, or plants are understood to encompass not only the end product of a transformation process, but also transgenic progeny thereof.

Transgenic: stably transformed with a recombinant DNA molecule that preferably comprises a suitable promoter operatively linked to a DNA sequence of interest.

BRIEF DESCRIPTION OF THE SEQUENCES IN THE SEQUENCE LISTING

SEQ ID NO:1 Genomic DNA, single exon, coding sequence for the Arabidopsis thaliana 8388 gene SEQ ID NO:2 amino acid sequence encoded by the Arabidopsis thaliana 8388 DNA sequence shown in SEQ ID NO:1

SEQ ID NO:3 complete cDNA sequence, including 5' UTR, coding region, and 3' UTR sequences, for the Arabidopsis thaliana 8388 gene SEQ ID NO:4 amino acid sequence encoded by the Arabidopsis thaliana 8388 cDNA sequence shown in SEQ ID NO:3

SEQ ID NO:5 cDNA coding sequence for the Arabidopsis thaliana 18048 gene

SEQ ID NO:6 amino acid sequence encoded by the Arabidopsis thaliana 18048 DNA sequence shown in SEQ ID NO:5

SEQ ID NO:7 cDNA coding sequence for the Arabidopsis thaliana 16713 gene

SEQ ID NO:8 amino acid sequence encoded by the Arabidopsis thaliana 16713 DNA sequence shown in SEQ ID NO:7

SEQ ID NO:9 oligonucleotide CA50
SEQ ID NO:10 oligonucleotide CA51
SEQ ID NO:11 oligonucleotide CA52
SEQ ID NO:12 oligonucleotide CA53
SEQ ID NO:13 oligonucleotide CA54
SEQ ID NO:14 oligonucleotide CA55
SEQ ID NO:15 oligonucleotide CA66
SEQ ID NO:16 oligonucleotide CA67
SEQ ID NO:17 oligonucleotide CA68
SEQ ID NO:18 oligonucleotide JM33
SEQ ID NO:19 oligonucleotide JM34
SEQ ID NO:20 oligonucleotide JM35
SEQ ID NO:21 cDNA coding sequence for the Arabidopsis 4144 gene
SEQ ID NO:22 amino acid sequence encoded by the Arabidopsis 4144 DNA sequence shown in SEQ ID NO:21
SEQ ID NO:23 genomic sequence of the Arabidopsis 4144 gene
SEQ ID NO:24 5' UTR from the cDNA sequence for the Arabidopsis 4144 gene
SEQ ID NO:25 3' UTR from the cDNA sequence for the Arabidopsis 4144 gene
SEQ ID NO:26 oligonucleotide slp346

DETAILED DESCRIPTION OF THE INVENTION

I.a. Essentiality of the 8388, 18048, and 16713 Genes in *Arabidopsis thaliana* Demonstrated by T-DNA Insertion Mutagenesis As shown in the examples below, the identification of a novel gene structure, as well as the essentiality of the 8388, 18048, and 16713 genes for normal plant growth and development, have been demonstrated for the first time in Arabidopsis using T-DNA insertion mutagenesis. Having established the essentiality of 8388, 18048, and 16713 function in plants and having identified the genes encoding these essential activities, the inventors thereby provide an important and sought after tool for new herbicide development.

Essential genes are identified through the isolation of lethal mutants blocked in early development. Examples of lethal mutants include those blocked in the formation of the male or female gametes or embryo. Gametophytic mutants are found by examining T1 insertion lines for the presence of 50% aborted pollen grains or ovules. Embryo defective mutants produce 25% defective seeds following self-pollination of T1 plants (see Errampalli et al. 1991, Plant Cell 3:149–157; Castle et al. 1993, Mol Gen Genet 241:504–514).

When a line is identified as segregating for an embryo lethal mutation, it is determined if the resistance marker in the T-DNA co-segregates with the lethality (Errampalli et al. (1991) The Plant Cell, 3:149–157). Cosegregation analysis is done by placing the seeds on media containing the selective agent and scoring the seedlings for resistance or sensitivity to the agent. Examples of selective agents used are hygromycin or phosphinothricin. About 35 (8388), 35 (18048), and 38 (16713) resistant seedlings are transplanted to soil and their progeny are examined for the segregation of the embryo-lethal phenotype. In the case in which the T-DNA insertion disrupts an essential gene, there is cosegregation of the resistance phenotype and the embryo-lethal phenotype in every plant. Therefore, in such a case, all resistant plants segregate for the lethal phenotype in the next generation; this result indicates that each of the resistant plants is heterozygous for the mutation and hemizygous for the T-DNA insert causing the mutation. For those lines showing cosegregation of the T-DNA resistance marker and the lethal phenotype, PCR-based approaches, such as TAIL PCR (Liu and Whittier (1995), Genomics, 25: 674–681) vectorette PCR (Riley et al. (1990) Nucleic Acids Research, 18: 2887–2890), or a strategy such as the Genome Walker system (CLONTECH Laboratories, Inc, Palo Alto, Calif.), may be used to directly amplify plant DNA/T-DNA border fragments. Each of these techniques takes advantage of the fact that the DNA sequence of the insertion element is known, and can routinely be used to recover small (less than 5 kb) fragments adjacent to the known sequence. Alternatively, plasmid rescue may be used to isolate the plant DNA/T-DNA border fragments. Southern blot analysis may be performed as an initial step in the characterization of the molecular nature of each insertion. Southern blots are done with genomic DNA isolated from heterozygotes and using probes capable of hybridizing with the T-DNA vector DNA.

Using the results of the Southern analysis, appropriate restriction enzymes are chosen to perform plasmid rescue in order to molecularly clone *Arabidopsis thaliana* genomic DNA flanking one or both sides of the T-DNA insertion. Plasmids obtained in this manner are analyzed by restriction enzyme digestion to sort the plasmids into classes based on their digestion pattern. For each class of plasmid clone, the DNA sequence is determined.

The resulting sequences, obtained by any of the above outlined approaches, are analyzed for the presence of non-T-DNA vector sequences. When such sequences are found, they are used to search DNA and protein databases using the BLAST and BLAST2 programs (Altschul et al. (1990) J Mol. Biol. 215: 403–410; Altschul et al (1997) Nucleic Acid Res. 25:3389–3402). Additional genomic and cDNA sequences for each gene are identified by standard molecular biology procedures.

One method of confirming that the disrupted gene is the cause of the mutant phenotype is to transform a wild-type form of the gene into the mutant plant. Another method is identification of a second mutant allele showing a lethal phenotype. Alternatively, the mutant is phenocopied by specifically reducing expression of the disrupted gene in transgenic plants expressing an antisense version of the gene behind a synthetic promoter (Guyer et al. (1998) Genetics, 149: 633–639). Thus, for example, two other revertant alleles disrupting the 8388 gene are obtained by T-DNA insertion (mutants no. 14652 and 29863). Also, another mutant allele of the 18048 gene is obtained by EMS mutagenesis (mutant no. ttn5–2 with a mutation at base 195 of the coding sequence changing a Trp codon (TGG) to a stop codon (TGA)).

I.b. Essentiality of the 4144 Gene in Arabidopsis Demonstrated by T-DNA Insertion Mutagenesis As shown in the examples below, the identification of a novel gene structure, as well as the essentiality of the 4144 gene for normal plant growth and development, have been demonstrated for the first time in Arabidopsis using T-DNA insertion mutagenesis. Having established the essentiality of 4144 function in plants and having identified the gene encoding this essential activity, the inventors thereby provide an important and sought after tool for new herbicide development.

Arabidopsis insertional mutant lines segregating for seedling lethal mutations are identified as a first step in the identification of essential proteins. Starting with T2 seeds collected from single T1 plants containing T-DNA insertions in their genomes, those lines segregating homozygous seedling lethal seedlings are identified. These lines are found by placing seeds onto minimal plant growth media, which contains the fungicides benomyl and maxim, and screening for inviable seedlings after 7 and 14 days in the light at room temperature. Inviable phenotypes include altered pigmentation or altered morphology. These phenotypes are observed either on plates directly or in soil following transplantation of seedlings.

When a line is identified as segregating a seedling lethal, it is determined if the resistance marker in the T-DNA co-segregates with the lethality (Errampalli et al. (1991) The Plant Cell, 3:149–157). Co-segregation analysis is done by placing the seeds on media containing the selective agent and scoring the seedlings for resistance or sensitivity to the agent. Examples of selective agents used are hygromycin or phosphinothricin. About 35 resistant seedlings are transplanted to soil and their progeny are examined for the segregation of the seedling lethal. In the case in which the T-DNA insertion disrupts an essential gene, there is co-segregation of the resistance phenotype and the seedling lethal phenotype in every plant. Therefore, in such a case, all resistant plants segregate seedling lethals in the next generation; this result indicates that each of the resistant plants is heterozygous for the DNA causing both phenotypes.

For those lines showing co-segregation of the T-DNA resistance marker and the seedling lethal phenotype, Southern analysis is performed as an initial step in the characterization of the molecular nature of each insertion. Southerns are done with genomic DNA isolated from heterozygotes and using probes capable of hybridizing with the T-DNA vector DNA. Using the results of the Southern analysis, appropriate restriction enzymes are chosen to perform plasmid rescue in order to molecularly clone Arabidopsis genomic DNA flanking one or both sides of the T-DNA insertion. Plasmids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequences. When such sequences are found, they are used to search DNA and protein databases using the BLAST and BLAST2 programs (Altschul et al. (1990) J Mol. Biol. 215: 403–410; Altschul et al (1997) Nucleic Acid Res. 25:3389–3402). Additional genomic and cDNA sequences for each gene are identified by standard molecular biology procedures.

II. Sequence of the Arabidopsis 8388, 18048, 16713 and 4144 Genes

The Arabidopsis 8388 gene is identified by isolating DNA flanking the T-DNA border from the tagged embryo-lethal line #8388. Arabidopsis DNA flanking the T-DNA border is identical to regions of two sequenced EST clones from Arabidopsis (accession numbers H77096 and R30603). The inventors are the first to demonstrate that the 8388 gene product is essential for normal growth and development in plants, as well as defining the function of the 8388 gene product through protein homology. The present invention discloses the cDNA nucleotide sequence of the Arabidopsis 8388 gene as well as the amino acid sequence of the Arabidopsis 8388 protein. The nucleotide sequence corresponding to the genomic DNA, single exon, coding region is set forth in SEQ ID NO:1, and the amino acid sequence encoding the protein is set forth in SEQ ID NO:2. The nucleotide sequence corresponding to the complete cDNA, which includes 5' UTR and coding and 3' UTR sequences, is set forth in SEQ ID NO:3. The present invention also encompasses an isolated amino acid sequence derived from a plant, wherein said amino acid sequence is identical or substantially similar to the amino acid sequence encoded by the nucleotide sequence set forth in SEQ ID NO:1, wherein said amino acid sequence has 8388 activity. Using BLASTX (2.0.7) programs with the default settings, the sequence of the 8388 gene shows similarity to DEAD box RNA helicase. Notable species similarities include: human EIF-4A-I [Genbank peptide accession #417180]; mouse EIF-4A [Genbank peptide accession #72888]; mouse EIF-4A-I [Genbank peptide accession #90965]; and rabbit EIF-4A-I [Genbank peptide accession #266336].

The Arabidopsis 18048 gene is identified by isolating DNA flanking the T-DNA border from the tagged embryo-lethal line #18048. Arabidopsis DNA flanking the T-DNA border is identical to a sequenced BAC clone (T30D6, accession number AC006439). The inventors are the first to demonstrate that the 18048 gene product is essential for normal growth and development in plants, as well as defining the function of the 18048 gene product through protein homology. The present invention discloses the cDNA nucleotide sequence of the Arabidopsis 18048 gene as well as the amino acid sequence of the Arabidopsis 18048 protein. The nucleotide sequence corresponding to the cDNA coding region is set forth in SEQ ID NO:5, and the amino acid sequence encoding the protein is set forth in SEQ ID NO:6. The present invention also encompasses an isolated amino acid sequence derived from a plant, wherein said amino acid sequence is identical or substantially similar to the amino acid sequence encoded by the nucleotide sequence set forth in SEQ ID NO:5, wherein said amino acid sequence has 18048 activity. Using BLASTX (2.0.8) programs with the default settings, the sequence of the 18048 gene shows similarity to ADP-ribosylation factor genes. Notable species similarities include: human [accession #NP_001658], rat [accession #O08697], Drosophila [accession #Q06849], Caenorhabditis elegans [accession #CAA90353], Schizosaccharomyces pombe [accession #Q09767], maize [accession #P49076], and soybean [accession number AAD17207].

The Arabidopsis 16713 gene is identified by isolating DNA flanking the T-DNA border from the tagged embryo-lethal line #16713. Arabidopsis DNA flanking the T-DNA border is identical to a portion of sequence to the P1 clone MIF21 (Accession #AB023039). Annotation suggests that a gene is present in the region disrupted by the T-DNA. BLAST-N searches using default settings, using the annotated gene region, reveals public EST clones with sequence identity to the predicted gene, indicating that this region contains an expressed gene. The EST clones are: 144H12T7, 184O20T7, 126L22T7, VBVWD08, 204J9T7, 129A14, and 174A7T7. The inventors are the first to demonstrate that the 16713 gene product is essential for normal growth and development in plants, as well as defining the function of the 16713 gene product through protein homology. The present invention discloses the cDNA nucleotide sequence of the Arabidopsis 16713 gene as well as the amino acid sequence of the Arabidopsis 16713 protein. The nucleotide sequence corresponding to the cDNA coding region is set forth in SEQ ID NO:7, and the amino acid sequence encoding the protein is set forth in SEQ ID NO:8. The present invention also encompasses an isolated amino acid sequence derived from a plant, wherein said amino acid sequence is identical or substantially similar to the amino acid sequence encoded by the nucleotide sequence set forth in SEQ ID NO:1, wherein said amino acid sequence has 16713 activity. Using BLASTX (1.4.11) programs with the default settings, the sequence of the 16713 gene shows similarity to acetoacetyl coA thiolase genes. Notable species similarities include: radish (accession #CAA55006), maize (accession #AAD44539), yeast (accession #P41338), human (accession #BAA14278), rat (accession #BAA03016), Caenorhabditis elegans (accession #AAA82403), and E. coli (accession number Q46939).

The Arabidopsis 4144 gene is identified by isolating DNA flanking the T-DNA border from the tagged seedling-lethal line #4144. A region of the Arabidopsis DNA flanking the T-DNA border shows 100% identity to preliminary Arabidopsis genomic sequence (designated: Preliminary CSHL076 T25P22-99.03.10-68148.seq; found at http://genome-www2.stanford.edu/cgi-bin/AtDB/getseq?database=cshlprel&item=CSHL076). The inventors are the first to demonstrate that the 4144 gene product is essential for normal growth and development in plants, as well as defining the function of the 4144 gene through protein homology. The present invention discloses the cDNA coding nucleotide sequence of the Arabidopsis 4144 gene as well as the amino acid sequence of the Arabidopsis 4144 protein. The nucleotide sequence corresponding to the genomic DNA is set forth in SEQ ID NO:23.

III. Recombinant Production of 8388, 18048, 16713, and 4144 Activities and Uses Thereof For recombinant production of 8388, 18048, 16713, or 4144 activity in a host organism, a nucleotide sequence encoding a protein having one of the above activities is inserted into an expression cassette designed for the chosen host and introduced into the host where it is recombinantly produced. For example, SEQ ID NO:1, or nucleotide sequences substantially similar to SEQ ID NO:1, or homologs of the 8388 coding sequence can be used for the recombinant production of a protein having 8388 activity. For example, SEQ ID NO:5, or nucleotide sequences substantially similar to SEQ ID NO:5, or homologs of the 18048 coding sequence can be used for the recombinant production of a protein having 18048 activity. For example, SEQ ID NO:7, or nucleotide sequences substantially similar to SEQ ID NO:7, or homologs of the 16713 coding sequence can be used for the recombinant production of a protein having 16713 activity. For example, SEQ ID NO:21, or nucleotide sequences substantially similar to SEQ ID NO:21, or homologs of the 4144 coding sequence can be used for the recombinant production of a protein having 4144 activity. The choice of specific regulatory sequences such as promoter, signal sequence, 5' and 3' untranslated sequences, and enhancer appropriate for the chosen host is within the level of skill of the routineer in the art. The resultant molecule, containing the individual elements operably linked in proper reading frame, may be inserted into a vector capable of being transformed into the host cell. Suitable expression vectors and methods for recombinant production of proteins are well known for host organisms such as E. coli, yeast, and insect cells (see, e.g., Luckow and Summers, Bio/Technol. 6: 47 (1988), and baculovirus expression vectors, e.g., those derived from the genome of Autographica californica nuclear polyhedrosis virus (AcMNPV). A preferred baculovirus/insect system is pAcHLT (Pharmingen, San Diego, Calif.) used to transfect Spodoptera frugiperda Sf9 cells (ATCC) in the presence of linear Autographa californica baculovirus DNA (Pharmigen, San Diego, Calif.). The resulting virus is used to infect HighFive Tricoplusia ni cells (Invitrogen, La Jolla, Calif.).

In a preferred embodiment, the nucleotide sequence encoding a protein having 8388, 18048, 16713, or 4144 activity is derived from an eukaryote, such as a mammal, a fly or a yeast, but is preferably derived from a plant. In a further preferred embodiment, the nucleotide sequence is identical or substantially similar to the nucleotide sequence set forth in SEQ ID NO:1, SEQ ID NO:5, SEQ ID NO:7 or SEQ ID NO:21, respectively, or encodes a protein having 8388, 18048, 16713, or 4144 activity, respectively, whose amino acid sequence is identical or substantially similar to the amino acid sequence set forth in SEQ ID NO:2, SEQ ID NO:6, SEQ ID NO:8, or SEQ ID NO:22, respectively. The nucleotide sequence set forth in SEQ ID NO:1 encodes the Arabidopsis 8388 protein, whose amino acid sequence is set forth in SEQ ID NO:2. The nucleotide sequence set forth in SEQ ID NO:5 encodes the Arabidopsis 18048 protein, whose amino acid sequence is set forth in SEQ ID NO:6. The nucleotide sequence set forth in SEQ ID NO:7 encodes the Arabidopsis 16713 protein, whose amino acid sequence is set forth in SEQ ID NO:8. The nucleotide sequence set forth in SEQ ID NO:21 encodes the Arabidopsis 4144 protein, whose amino acid sequence is set forth in SEQ ID NO:22. In another preferred embodiment, the nucleotide sequences are derived from a prokaryote, preferably a bacteria, e.g. *E. coli*. Recombinantly produced protein having 8388, 18048, 16713, or 4144 activity is isolated and purified using a variety of standard techniques. The actual techniques that may be used will vary depending upon the host organism used, whether the protein is designed for secretion, and other such factors familiar to the skilled artisan (see, e.g. chapter 16 of Ausubel, F. et al., "Current Protocols in Molecular Biology", pub. by John Wiley & Sons, Inc. (1994).

Assays Utilizing the 8388, 18048, 16713, or 4144 Protein

Recombinantly produced 8388, 18048, 16713, or 4144 proteins having 8388, 18048, 16713, or 4144 activities, respectively, are useful for a variety of purposes. For example, they can be used in in vitro assays to screen known herbicidal chemicals whose target has not been identified to determine if they inhibit 8388, 18048, 16713, or 4144. Such in vitro assays may also be used as more general screens to identify chemicals that inhibit such enzymatic activity and that are therefore novel herbicide candidates. Alternatively, recombinantly produced 8388, 18048, 16713, or 4144 proteins having 8388, 18048, 16713, or 4144 activity may be used to elucidate the complex structure of these molecules and to further characterize their association with known inhibitors in order to rationally design new inhibitory herbicides as well as herbicide tolerant forms of the enzymes.

In vitro Inhibitor Assay

An in vitro assay usefiul for identifying inhibitors of enzymes encoded by essential plant genes, such as, e.g. 3-ketoacyl-CoA thiolase, comprises the steps of: a) reacting an enzyme, e.g. an enzyme having 3-ketoacyl-CoA thiolase activity and the substrate thereof in the presence of a suspected inhibitor of the enzyme's function; b) comparing the rate of enzymatic activities in the presence of the suspected inhibitor to the rate of enzymatic activities under the same conditions in the absence of the suspected inhibitor; and c) determining whether the suspected inhibitor inhibits the enzyme activity, e.g. the 3-ketoacyl-CoA thiolase activity. The inhibitory effect, e.g. on 3-ketoacyl-CoA thiolase, is determined by a reduction or complete inhibition of product formation in the assay. In a preferred embodiment, such a determination is made by comparing, in the presence and absence of the candidate inhibitor, the amount of product formed in the in vitro assay using fluorescence or absorbance detection. A preferred substrate for 3-ketoacyl-CoA thiolase is Acetoacetyl-CoA (AcAc-CoA). Additional substrates include palmitoyl coenzyme A, myristoyl coenzyme A, or lauroyl coenzyme A.

In vitro Inhibitor Assays: Discovery of Small Molecule Ligand that Interacts with the Gene Product of SEQ ID NO:1, SEQ ID NO:5, SEQ ID NO:7, or SEQ ID NO:21

Once a protein has been identified as a potential herbicide target, the next step is to develop an assay that allows screening large number of chemicals to determine which ones interact with the protein. Although it is straightforward to develop assays for proteins of known function, developing assays with proteins of unknown functions is more difficult.

This difficulty can be overcome by using technologies that can detect interactions between a protein and a compound without knowing the biological function of the protein. A short description of three methods is presented, including fluorescence correlation spectroscopy, surface-enhanced laser desorption/ionization, and biacore technologies.

Fluorescence Correlation Spectroscopy (FCS) theory was developed in 1972 but it is only in recent years that the technology to perform FCS became available (Madge et al. (1972) Phys. Rev. Lett., 29: 705–708; Maiti et al. (1997) Proc. Natl. Acad. Sci. USA, 94: 11753–11757). FCS measures the average diffusion rate of a fluorescent molecule within a small sample volume. The sample size can be as low as $10^3$ fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analyzed is expressed as a recombinant protein with a sequence tag, such as a poly-histidine sequence, inserted at the N or C-terminus. The expression takes place in *E. coli*, yeast or insect cells. The protein is purified by chromatography. For example, the poly-histidine tag can be used to bind the expressed protein to a metal chelate column such as Ni2+ chelated on iminodiacetic acid agarose. The protein is then labeled with a fluorescent tag such as carboxytetramethyl-rhodamine or BODIPY® (Molecular Probes, Eugene, Oreg.). The protein is then exposed in solution to the potential ligand, and its diffusion rate is determined by FCS using instrumentation available from Carl Zeiss, Inc. (Thornwood, N.Y.). Ligand binding is determined by changes in the diffusion rate of the protein.

Surface-Enhanced Laser Desorption/Ionization (SELDI) was invented by Hutchens and Yip during the late 1980's (Hutchens and Yip (1993) Rapid Commun. Mass Spectrom. 7: 576–580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules that bind to this protein (Worrall et al. (1998) Anal. Biochem. 70: 750–756). In a typical experiment, the target to be analyzed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system capable to pipet the ligands in a sequential manner (autosampler). The chip is then submitted to washes of increasing stringency, for example a series of washes with buffer solutions containing an increasing ionic strength. After each wash, the bound material is analyzed by submitting the chip to SELDI-TOF. Ligands that specifically bind the target will be identified by the stringency of the wash needed to elute them.

Biacore relies on changes in the refractive index at the surface layer upon binding of a ligand to a protein immobilized on the layer. In this system, a collection of small ligands is injected sequentially in a 2–5 microlitre cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299–304; Malmquist (1993) Nature, 361: 186–187). In a typical experiment, the target to be analyzed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

IV. In vivo Inhibitor Assay

In one embodiment, a suspected herbicide, for example identified by in vitro screening, is applied to plants at various concentrations. The suspected herbicide is preferably sprayed on the plants. After application of the suspected herbicide, its effect on the plants, for example death or suppression of growth is recorded.

In another embodiment, an in vivo screening assay for inhibitors of the 8388, 18048, 16713, or 4144 activity uses transgenic plants, plant tissue, plant seeds or plant cells capable of overexpressing a nucleotide sequence having 8388, 18048, 16713, or 4144 activity, wherein the 8388, 18048, 16713, or 4144 gene product is enzymatically active in the transgenic plants, plant tissue, plant seeds or plant cells. The nucleotide sequence is preferably derived from an eukaryote, such as a yeast, but is preferably derived from a plant. In a further preferred embodiment, the nucleotide sequence is identical or substantially similar to the nucleotide sequence set forth in SEQ ID NO:1, or encodes an enzyme having 8388 activity, whose amino acid sequence is identical or substantially similar to the amino acid sequence set forth in SEQ ID NO:2. In a further preferred embodiment, the nucleotide sequence is identical or substantially similar to the nucleotide sequence set forth in SEQ ID NO:5, or encodes an enzyme having 18048 activity, whose amino acid sequence is identical or substantially similar to the amino acid sequence set forth in SEQ ID NO:6. In a further preferred embodiment, the nucleotide sequence is identical or substantially similar to the nucleotide sequence set forth in SEQ ID NO:7, or encodes an enzyme having 16713 activity, whose amino acid sequence is identical or substantially similar to the amino acid sequence set forth in SEQ ID NO:8. In a further preferred embodiment, the nucleotide sequence is identical or substantially similar to the nucleotide sequence set forth in SEQ ID NO:21, or encodes an enzyme having 4144 activity, whose amino acid sequence is identical or substantially similar to the amino acid sequence set forth in SEQ ID NO:22. In another preferred embodiment, the nucleotide sequence is derived from a prokaryote, preferably a bacteria, e.g. *E. coli.*

A chemical is then applied to the transgenic plants, plant tissue, plant seeds or plant cells and to the isogenic non-transgenic plants, plant tissue, plant seeds or plant cells, and the growth or viability of the transgenic and non-transformed plants, plant tissue, plant seeds or plant cells arc determined after application of the chemical and compared. Compounds capable of inhibiting the growth of the non-transgenic plants, but not affecting the growth of the transgenic plants are selected as specific inhibitors of 8388, 18048, 16713, or 4144 activity.

V. Herbicide Tolerant Plants

The present invention is further directed to plants, plant tissue, plant seeds, and plant cells tolerant to herbicides that inhibit the naturally occurring 8388, 18048, 16713, or 4144 activity in these plants, wherein the tolerance is conferred by an altered 8388, 18048, 16713, or 4144 activity. Altered 8388, 18048, 16713, or 4144 activity may be conferred upon a plant according to the invention by increasing expression of wild-type herbicide-sensitive 8388, 18048, 16713, or 4144 gene, for example by providing additional wild-type 8388, 18048, 16713, or 4144 genes and/or by overexpressing the endogenous 8388, 18048, 16713, or 4144 gene, for example by driving expression with a strong promoter. Altered 8388, 18048, 16713, or 4144 activity also may be accomplished by expressing nucleotide sequences that are substantially similar to SEQ ID NO:1, SEQ ID NO:5, SEQ ID NO:7, or SEQ ID NO:21, respectively, or homologs in a plant. Still further altered 8388, 18048, 16713, or 4144 activity is conferred on a plant by expressing modified herbicide-tolerant 8388, 18048, 16713, or 4144 genes in the plant. Combinations of these techniques may also be used. Representative plants include any plants to which these herbicides are applied for their normally intended purpose. Preferred are agronomically important crops such as cotton, soybean, oilseed rape, sugar beet, maize, rice, wheat, barley, oats, rye, sorghum, millet, turf, forage, turf grasses, and the like.

A. Increased Expression of Wild-Type 8388, 18048, 16713, or 4144

Achieving altered 8388, 18048, 16713, or 4144 activity through increased expression results in a level of 8388, 18048, 16713, or 4144 activity in the plant cell at least sufficient to overcome growth inhibition caused by the herbicide when applied in amounts sufficient to inhibit normal growth of control plants. The level of expressed enzyme generally is at least two times, preferably at least five times, and more preferably at least ten times the natively expressed amount. Increased expression may be due to multiple copies of a wild-type 8388, 18048, 16713, or 4144 gene; multiple occurrences of the coding sequence within the gene (i.e. gene amplification) or a mutation in the non-coding, regulatory sequence of the endogenous gene in the plant cell. Plants having such altered gene activity can be obtained by direct selection in plants by methods known in the art (see, e.g. U.S. Pat. No. 5,162,602, and U.S. Pat. No. 4,761,373, and references cited therein). These plants also may be obtained by genetic engineering techniques known in the art. Increased expression of a herbicide-sensitive 8388, 18048, 16713, or 4144 gene can also be accomplished by transforming a plant cell with a recombinant or chimeric DNA molecule comprising a promoter capable of driving expression of an associated structural gene in a plant cell operatively linked to a homologous or heterologous structural gene encoding the 8388, 18048, 16713, or 4144 protein or a homolog thereof. Preferably, the transformation is stable, thereby providing a heritable transgenic trait.

B. Expression of Modified Herbicide-Tolerant 8388, 18048, 16713, or 4144 Proteins According to this embodiment, plants, plant tissue, plant seeds, or plant cells are stably transformed with a recombinant DNA molecule comprising a suitable promoter functional in plants operatively linked to a coding sequence encoding a herbicide tolerant form of the 8388, 18048, 16713, or 4144 protein. A herbicide tolerant form of the enzyme has at least one amino acid substitution, addition or deletion that confers tolerance to a herbicide that inhibits the unmodified, naturally occurring form of the enzyme. The transgenic plants, plant tissue, plant seeds, or plant cells thus created are then selected by conventional selection techniques, whereby herbicide tolerant lines are isolated, characterized, and developed. Below are described methods for obtaining genes that encode herbicide tolerant forms of 8388, 18048, 16713, or 4144 protein.

One general strategy involves direct or indirect mutagenesis procedures on microbes. For instance, a genetically manipulatable microbe such as *E. coli* or *S. cerevisiae* may be subjected to random mutagenesis in vivo with mutagens such as UV light or ethyl or methyl methane sulfonate. Mutagenesis procedures are described, for example, in Miller, *Experiments in Molecular Genetics*, Cold Spring Harbor Laboratory, Cold Spring Harbor, N.Y. (1972); Davis et al., *Advanced Bacterial Genetics*, Cold Spring Harbor Laboratory, Cold Spring Harbor, N.Y. (1980); Sherman et al., *Methods in Yeast Genetics*, Cold Spring Harbor Laboratory, Cold Spring Harbor, N.Y. (1983); and U.S. Pat. No. 4,975,374. The microbe selected for mutagenesis contains a normal, inhibitor-sensitive 8388, 18048, 16713, or 4144 gene and is dependent upon the activity conferTed by this gene. The mutagenized cells are grown in the presence of the inhibitor at concentrations that inhibit the unmodified gene. Colonies of the mutagenized microbe that grow better than the unmutagenized microbe in the presence of the inhibitor (i.e. exhibit resistance to the inhibitor) are selected for further analysis. 8388, 18048, 16713, or 4144 genes conferring tolerance to the inhibitor are isolated from these colonies, either by cloning or by PCR amplification, and their sequences are elucidated. Sequences encoding altered gene products are then cloned back into the microbe to confirm their ability to confer inhibitor tolerance.

A method of obtaining mutant herbicide-tolerant alleles of a plant 8388, 18048, 16713, or 4144 gene involves direct selection in plants. For example, the effect of a mutagenized 8388, 18048, 16713, or 4144 gene on the growth inhibition of plants such as Arabidopsis, soybean, or maize is determined by plating seeds sterilized by art-recognized methods on plates on a simple minimal salts medium containing increasing concentrations of the inhibitor. Such concentrations are in the range of 0.001, 0.003, 0.01, 0.03, 0.1, 0.3, 1, 3, 10, 30, 110, 300, 1000 and 3000 parts per million (ppm). The lowest dose at which significant growth inhibition can be reproducibly detected is used for subsequent experiments. Determination of the lowest dose is routine in the art.

Mutagenesis of plant material is utilized to increase the frequency at which resistant alleles occur in the selected population. Mutagenized seed material is derived from a variety of sources, including chemical or physical mutagenesis or seeds, or chemical or physical mutagenesis or pollen (Neuffer, In *Maize for Biological Research* Sheridan, ed. Univ. Press, Grand Forks, N.Dak., pp. 61–64 (1982)), which is then used to fertilize plants and the resulting $M_1$ mutant seeds collected. Typically for Arabidopsis, $M_2$ seeds (Lehle Seeds, Tucson, Ariz.), which are progeny seeds of plants grown from seeds mutagenized with chemicals, such as ethyl methane sulfonate, or with physical agents, such as gamma rays or fast neutrons, are plated at densities of up to 10,000 seeds/plate (10 cm diameter) on minimal salts medium containing an appropriate concentration of inhibitor to select for tolerance. Seedlings that continue to grow and remain green 7–21 days after plating are transplanted to soil and grown to maturity and seed set. Progeny of these seeds are tested for tolerance to the herbicide. If the tolerance trait is dominant, plants whose seed segregate 3:1/resistant:sensitive are presumed to have been heterozygous for the resistance at the $M_2$ generation. Plants that give rise to all resistant seed are presumed to have been homozygous for the resistance at the $M_2$ generation. Such mutagenesis on intact seeds and screening of their M2 progeny seed can also be carried out on other species, for instance soybean (see, e.g. U.S. Pat. No. 5,084,082). Alternatively, mutant seeds to be screened for herbicide tolerance are obtained as a result of fertilization with pollen mutagenized by chemical or physical means.

Confirmation that the genetic basis of the herbicide tolerance is a 8388, 18048, 16713, or 4144 gene is ascertained as exemplified below. First, alleles of the 8388, 18048, 16713, or 4144 gene from plants exhibiting resistance to the inhibitor are isolated using PCR with primers based either upon the Arabidopsis cDNA coding sequences shown in SEQ ID NO:1, SEQ ID NO:5, SEQ ID NO:7, or SEQ ID NO:21, respectively, or, more preferably, based upon the unaltered 8388, 18048, 16713, or 4144 gene sequence from the plant used to generate tolerant alleles. After sequencing the alleles to determine the presence of mutations in the coding sequence, the alleles are tested for their ability to confer tolerance to the inhibitor on plants into which the putative tolerance-conferring alleles have been transformed. These plants can be either Arabidopsis plants or any other plant whose growth is susceptible to the 8388, 18048, 16713, or 4144 inhibitors. Second, the inserted 8388, 18048, 16713, or 4144 genes are mapped relative to known restriction fragment length polymorphisms (RFLPs) (See, for example, Chang et al. *Proc. Natl. Acad, Sci, USA* 85: 6856–6860 (1988); Nam et al., *Plant Cell* 1: 699–705 (1989), cleaved amplified polymorphic sequences (CAPS) (Konieczny and Ausubel (1993) The Plant Journal, 4(2): 403–410), or SSLPs (Bell and Ecker (1994) Genomics, 19: 137–144). The 8388, 18048, 16713, or 4144 inhibitor tolerance trait is independently mapped using the same markers. When tolerance is due to a mutation in that 8388, 18048, 16713, or 4144 gene, the tolerance trait maps to a position indistinguishable from the position of the 8388, 18048, 16713, or 4144 gene.

Another method of obtaining herbicide-tolerant alleles of a 8388, 18048, 16713, or 4144 gene is by selection in plant cell cultures. Explants of plant tissue, e.g. embryos, leaf disks, etc. or actively growing calluis or suspension cultures of a plant of interest are grown on medium in the presence of increasing concentrations of the inhibitory herbicide or an analogous inhibitor suitable for use in a laboratory environment. Varying degrees of growth are recorded in different cultures. In certain cultures, fast-growing variant colonies arise that continue to grow even in the presence of normally inhibitory concentrations of inhibitor. The frequency with which such faster-growing variants occur can be increased by treatment with a chemical or physical mutagen before exposing the tissues or cells to the inhibitor. Putative tolerance-conferring alleles of the 8388, 18048, 16713, or 4144 gene are isolated and tested as described in the foregoing paragraphs. Those alleles identified as conferring herbicide tolerance may then be engineered for optimal expression and transformed into the plant. Alternatively, plants can be regenerated from the tissue or cell cultures containing these alleles.

Still another method involves mutagenesis of wild-type, herbicide sensitive plant 8388, 18048, 16713, or 4144 genes in bacteria or yeast, followed by culturing the microbe on medium that contains inhibitory concentrations (i.e. sufficient to cause abnormal growth, inhibit growth or cause cell death) of the inhibitor, and then selecting those colonies that grow normally in the presence of the inhibitor. More specifically, a plant cDNA, such as the Arabidopsis cDNA encoding the 8388, 18048, 16713, or 4144 protein, is cloned into a microbe that otherwise lacks the 8388, 18048, 16713, or 4144 activity. The transformed microbe is then subjected to in vivo mutagenesis or to in vitro mutagenesis by any of several chemical or enzymatic methods known in the art, e.g. sodium bisulfite (Shortle et al., *Methods Enzymol.* 100:457–468 (1983); methoxylamine (Kadonaga et al., *Nucleic Acids Res.* 13:1733–1745 (1985); oligonucleotide-directed saturation mutagenesis (Hutchinson et al., *Proc. Natl. Acacl. Sci. USA*, 83:710–714 (1986); or various polymerase misincorporation strategies (see, e.g. Shortle et al., Proc. Natl. Acad. Sci. USA, 79:1588–1592 (1982); Shiraishi et al., *Gene* 64:313–319 (1988); and Leung et al., *Technique* 1:11–15 (1989). Colonies that grow normally in the presence of normally inhibitory concentrations of inhibitor are picked and purified by repeated restreaking. Their plasmids are purified and tested for the ability to confer tolerance to the inhibitor by retransforming them into the microbe lacking 8388, 18048, 16713, or 4144 activity. The DNA sequences of cDNA inserts fromi plasmids that pass this test are then determined.

Herbicide resistant 8388, 18048, 16713, or 4144 proteins are also obtained using methods involving in vitro recombination, also called DNA shuffling. By DNA shuffling, mutations, preferably random mutations, are introduced into nucleotide sequences encoding 8388, 18048, 16713, or 4144 activity. DNA shuffling also leads to the recombination and rearrangement of sequences within a 8388, 18048, 16713, or 4144 gene or to recombination and exchange of sequences between two or more different of 8388, 18048, 16713, or 4144 genes. These methods allow for the production of millions of mutated 8388, 18048, 16713, or 4144 coding sequences. The mutated genes, or shuffled genes, are screened for desirable properties, e.g. improved tolerance to herbicides and for mutations that provide broad spectrum tolerance to the different classes of inhibitor chemistry. Such screens are well within the skills of a routineer in the art.

In a preferred embodiment, a mutagenized 8388, 18048, 16713, or 4144 gene is formed from at least one template 8388, 18048, 16713, or 4144 gene, wherein the template 8388, 18048, 16713, or 4144 gene has been cleaved into double-stranded random fragments of a desired size, and comprising the steps of adding to the resultant population of double-stranded random fragments one or more single or double-stranded oligonucleotides, wherein said oligonucleotides comprise an area of identity and an area of heterology to the double-stranded random fragments; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide, wherein the mutagenized polynucleotide is a mutated 8388, 18048, 16713, or 4144 gene having enhanced tolerance to a herbicide which inhibits naturally occurring 8388, 18048, 16713, or 4144 activity. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles. Such method is described e.g. in Stemmer et al. (1994) Nature 370: 389–391, in U.S. Pat. No. 5,605,793, U.S. Pat. No. 5,811,238 and in Crameri et al. (1998) Nature 391: 288–291, as well as in WO 97/20078, and these references are incorporated herein by reference.

In another preferred embodiment, any combination of two or more different 8388, 18048, 16713, or 4144 genes are mutagenized in vitro by a staggered extension process (StEP), as described e.g. in Zhao et al. (1998) Nature Biotechnology 16: 258–261. The two or more 8388, 18048, 16713, or 4144 genes are used as template for PCR amplification with the extension cycles of the PCR reaction preferably carried out at a lower temperature than the optimal polymerization temperature of the polymerase. For example, when a thermostable polymerase with an optimal temperature of approximately 72° C. is used, the temperature for the extension reaction is desirably below 72° C., more desirably below 65° C., preferably below 60° C., more preferably the temperature for the extension reaction is 55° C. Additionally, the duration of the extension reaction of the PCR cycles is desirably shorter than usually carried out in the art, more desirably it is less than 30 seconds, preferably it is less than 15 seconds, more preferably the duration of the extension reaction is 5 seconds. Only a short DNA fragment is polymerized in each extension reaction, allowing template switch of the extension products between the starting DNA molecules after each cycle of denaturation and annealing, thereby generating diversity among the extension products. The optimal number of cycles in the PCR reaction depends on the length of the 8388, 18048, 16713, or 4144 genes to be mutagenized but desirably over 40 cycles, more desirably over 60 cycles, preferably over 80 cycles are used. Optimal extension conditions and the optimal number of PCR cycles for every combination of 8388, 18048, 16713, or 4144 genes are determined as described in using procedures well-known in the art. The other parameters for the PCR reaction are essentially the same as commonly used in the art. The primers for the amplification reaction are preferably designed to anneal to DNA sequences located outside of the 8388, 18048, 16713, or 4144 genes, e.g. to DNA sequences of a vector comprising the 8388, 18048, 16713, or 4144 genes, whereby the different 8388, 18048, 16713, or 4144 genes used in the PCR reaction are preferably comprised in separate vectors. The primers desirably anneal to sequences located less than 500 bp away from 8388, 18048, 16713, or 4144 sequences, preferably less than 200 bp away from the 8388, 18048, 16713, or 4144 sequences, more preferably less than 120 bp away from the 8388, 18048, 16713, or 4144 sequences. Preferably, the 8388, 18048, 16713, or 4144 sequences are surrounded by restriction sites, which are included in the DNA sequence amplified during the PCR reaction, thereby facilitating the cloning of the amplified products into a suitable vector.

In another preferred embodiment, fragments of 8388, 18048, 16713, or 4144 genes having cohesive ends are produced as described in WO 98/05765. The cohesive ends are produced by ligating a first oligonucleotide corresponding to a part of a 8388, 18048, 16713, or 4144 gene to a second oligonucleotide not present in the gene or corresponding to a part of the gene not adjoining to the part of the gene corresponding to the first oligonucleotide, wherein the second oligonucleotide contains at least one ribonucleotide. A double-stranded DNA is produced using the first oligonucleotide as template and the second oligonucleotide as primer. The ribonucleotide is cleaved and removed. The nucleotide(s) located 5' to the ribonucleotide is also removed, resulting in double-stranded fragments having cohesive ends. Such fragments are randomly reassembled by ligation to obtain novel combinations of gene sequences.

In yet another embodiment, herbicide-resistant 8388, 18048, 16713, or 4144 proteins are produced using the incremental truncation for the creation of hybrid enzymes (ITCHY), as described in Ostermejer et al. (1999) Nature Biotechnology 17:1205–1209), and this reference is incorporated herein by reference.

Any 8388, 18048, 16713, or 4144 gene or any combination of 8388, 18048, 16713, or 4144 genes is used for in vitro recombination in the context of the present invention, for example, a 8388, 18048, 16713, or 4144 gene derived from a plant, such as, e.g. *Arabidopsis thaliana*, e.g. a 8388, 18048, 16713, or 4144 gene set forth in SEQ ID NO:1, SEQ ID NO:5, SEQ ID NO:7, or SEQ ID NO:21, respectively. A 8388-like gene from *E. coli*, yeast, human, or mouse (Luking et al. (1998) Critical Reviews in Biochemistry and Molecular Biology, 33 (4): 259–296), a 18048-like gene from human or Drosophila (Clark et al. (1993) Proc. Natl. Acad. Sci. U.S.A. 90 (19): 8952–8956 or other like genes), a 16713-like gene (Vollack and Bach (1996) Plant Physiol. 111: 1097–1107 or other like genes), all of which are incorporated herein by reference. Whole 8388, 18048, 16713, or 4144 genes or portions thereof are used in the context of the present invention. The library of mutated 8388, 18048, 16713, or 4144 genes obtained by the methods described above are cloned into appropriate expression vectors and the resulting vectors are transformed into an appropriate host, for example an algae like Chlamydomonas, a yeast or a bacteria. An appropriate host is preferably a host that otherwise lacks 8388, 18048, 16713, or 4144 activity, for example *E. coli*. Host cells transformed with the vectors comprising the library of mutated 8388, 18048, 16713, or 4144 genes are cultured on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

An assay for identifying a modified 8388, 18048, 16713, or 4144 gene that is tolerant to an inhibitor may be performed in the same manner as the assay to identify inhibitors of the 8388, 18048, 16713, or 4144 activity (Inhibitor Assay, above) with the following modifications: First, a mutant 8388, 18048, 16713, or 4144 protein is substituted in one of the reaction mixtures for the wild-type 8388, 18048, 16713, or 4144 protein of the inhibitor assay. Second, an inhibitor of wild-type enzyme is present in both reaction mixtures. Third, mutated activity (activity in the presence of inhibitor and mutated enzyme) and unmutated activity (activity in the presence of inhibitor and wild-type enzyme) are compared to determine whether a significant increase in enzymatic activity is observed in the mutated activity when compared to the unmutated activity. Mutated activity is any measure of activity of the mutated enzyme while in the presence of a suitable substrate and the inhibitor. Unmutated activity is any measure of activity of the wild-type enzyme while in the presence of a suitable substrate and the inhibitor.

In addition to being used to create herbicide-tolerant plants, genes encoding herbicide tolerant 8388, 18048, 16713, or 4144 protein can also be used as selectable markers in plant cell transformation methods. For example, plants, plant tissue, plant seeds, or plant cells transformed with a heterologous DNA sequence can also be transformed with a sequence encoding an altered 8388, 18048, 16713, or 4144 activity capable of being expressed by the plant. The transformed cells are transferred to medium containing an inhibitor of the enzyme in an amount sufficient to inhibit the growth or survivability of plant cells not expressing the modified coding sequence, wherein only the transformed cells will grow. The method is applicable to any plant cell capable of being transformed with a modified 8388, 18048, 16713, or 4144 gene, and can be used with any heterologous DNA sequence of interest. Expression of the heterologous DNA sequence and the modified gene can be driven by the same promoter functional in plant cells, or by separate promoters.

VI. Plant Transformation Technology

A wild-type or herbicide-tolerant form of the 8388, 18048, 16713, or 4144 gene, or homologs thereof, can be incorporated in plant or bacterial cells using conventional recombinant DNA technology. Generally, this involves inserting a DNA molecule encoding the 8388, 18048, 16713, or 4144 gene into an expression system to which the DNA molecule is heterologous (i.e., not normally present) using standard cloning procedures known in the art. The vector contains the necessary elements for the transcription and translation of the inserted protein-coding sequences in a host cell containing the vector. A large number of vector systems known in the art can be used, such as plasmids, bacteriophage viruses and other modified viruses. The components of the expression system may also be modified to increase expression. For example, truncated sequences, nucleotide substitutions, nucleotide optimization or other modifications may be employed. Expression systems known in the art can be used to transform virtually any crop plant cell under suitable conditions. A heterologous DNA sequence comprising a wild-type or herbicide-tolerant form of the 8388, 18048, 16713, or 4144 gene is preferably stably transformed and integrated into the genome of the host cells. In another preferred embodiment, the heterologous DNA sequence comprising a wild-type or herbicide-tolerant form of the 8388, 18048, 16713, or 4144 gene located on a self-replicating vector. Examples of self-replicating vectors are viruses, in particular gemini viruses. Transformed cells can be regenerated into whole plants such that the chosen form of the 8388, 18048, 16713, or 4144 gene confers herbicide tolerance in the transgenic plants.

A. Requirements for Construction of Plant Expression Cassettes

Gene sequences intended for expression in transgenic plants are first assembled in expression cassettes behind a suitable promoter expressible in plants. The expression cassettes may also comprise any further sequences required or selected for the expression of the heterologous DNA sequence. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes will determine the spatial and temporal expression pattern of the heterologous DNA sequence in the plant transformed with this DNA sequence. Selected promoters will express heterologous DNA sequences in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters known in the art can be used. For example, for constitutive expression, the CaMV 35S promoter, the rice actin promoter, or the ubiquitin promoter may be used. For regulatable expression, the chemically inducible PR-1 promoter from tobacco or Arabidopsis may be used (see, e.g., U.S. Pat. No. 5,689,044).

2. Transcriptional Terminators

A variety of transcriptional terminators are available for use in expression cassettes. These are responsible for the termination of transcription beyond the heterologous DNA sequence and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledonous and dicotyledonous plants.

3. Sequences for the Enhancement or Regulation of Expression

Numerous sequences have been found to enhance gene expression from within the transcriptional unit and these sequences can be used in conjunction with the genes of this invention to increase their expression in transgenic plants. For example, various intron sequences such as introns of the maize AdhI gene have been shown to enhance expression, particularly in monocotyledonous cells. In addition, a number of non-translated leader sequences derived from viruses are also known to enhance expression, and these are particularly effective in dicotyledonous cells.

4. Coding Sequence Optimization

The coding sequence of the selected gene may be genetically engineered by altering the coding sequence for optimal expression in the crop species of interest. Methods for modifying coding sequences to achieve optimal expression in a particular crop species are well known (see, e.g. Perlak et al., *Proc. Natl. Acaci. Sci. USA* 88: 3324 (1991); and Koziel et al, *Bio/technol*. 11: 194 (1993)).

5. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous products encoded by DNA sequences to these organelles. In addition, sequences have been characterized which cause the targeting of products encoded by DNA sequences to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et aL Plant Molec. Biol. 14: 357–368 (1990)). By the fusion of the appropriate targeting sequences described above to heterologous DNA sequences of interest it is possible to direct this product to any organelle or cell compartment.

B. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), the manA gene, which allows for positive selection in the presence of mannose (Miles and Guest (1984) Gene, 32:41–48; U.S. Pat. No. 5,767,378), and the dhfr gene, which confers resistance to methotrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)). Typical vectors suitable for Agrobacterium transformation include the binary vectors pCIB200 and pCIB2001, as well as the binary vector pCIB10 and hygromycin selection derivatives thereof. (See, for example, U.S. Pat. No. 5,639,949).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Typical vectors suitable for non-Agrobacterium transformation include pCIB3064, pSOG19, and pSOG35. (See, for example, U.S. Pat. No. 5,639,949).

C. Transformation Techniques

Once the coding sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells.

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG- or electroporation-mediated uptake, particle bombardment-mediated delivery, or microinjection. In each case the transformed cells are regenerated to whole plants using standard techniques known in the art.

Transformation of most monocotyledon species has now also become routine. Preferred techniques include direct gene transfer into protoplasts using PEG or electroporation techniques, particle bombardment into callus tissue, as well as Agrobacterium-mediated transformation.

D. Plastid Transformation

In another preferred embodiment, a nucleotide sequence encoding a polypeptide having 8388, 18048, 16713, or 4144 activity is directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit expression levels that can readily exceed 10% of the total soluble plant protein. In a preferred embodiment, the nucleotide sequence is inserted into a plastid targeting vector and transformed into the plastid genome of a desired plant host. Plants homoplasmic for plastid genomes containing the nucleotide sequence are obtained, and are preferentially capable of high expression of the nucleotide sequence.

Plastid transformation technology is for example extensively described in U.S. Pat. Nos. 5,451,513, 5,545,817, 5,545,818, and 5,877,462 in PCT application no. WO 95/16783 and WO 97/32977, and in McBride et al. (1994) Proc. Natl. Acad. Sci. USA 91, 7301–7305, all incorporated herein by reference in their entirety. The basic technique for plastid transformation involves introducing regions of cloned plastid DNA flanking a selectable marker together with the nucleotide sequence into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913–917). Other selectable markers useful for plastid transformation are known in the art and encompassed within the scope of the invention.

VII. Breeding

The wild-type or altered form of a 8388, 18048, 16713, or 4144 gene of the present invention can be utilized to confer herbicide tolerance to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, canot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The high-level expression of a wild-type 8388, 18048, 16713, or 4144 gene and/or the expression of herbicide-tolerant forms of a 8388, 18048, 16713, or 4144 gene conferring herbicide tolerance in plants, in combination with other characteristics important for production and quality, can be incorporated into plant lines through breeding approaches and techniques known in the art.

Where a herbicide tolerant 8388, 18048, 16713, or 4144 gene allele is obtained by direct selection in a crop plant or plant cell culture from which a crop plant can be regenerated, it is moved into commercial varieties using traditional breeding techniques to develop a herbicide tolerant crop without the need for genetically engineering the allele and transforming it into the plant.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, el al, *Molecular Cloning*, eds., Cold Spring Harbor Laboratory Press, Cold Spring Harbor, N.Y. (1989) and by T. J. Silhavy, M. L. Bermnan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987), Reiter, et al., *Methods in Arabidopsis Research*, World Scientific Press (1992), and Schultz et al., *Plant Molecular Biology Manual*, Kluwer Academic Publishers (1998). These references describe the standard techniques used for all steps in tagging and cloning genes from T-DNA mutagenized populations of Arabiclopsis: plant infection and transformation; screening for the identification of seedling mutants; cosegregation analysis; and plasmid rescue.

Example 1

Plant Infection and Transformation in Tagged Embryo-Lethal Lines 8388, 18048, and 16713

Arabidopsis plants (strain Columbia) are inverted, and their leaves are vacuum-infiltrated with Agrobacterium (1× dilution of Agrobacterium grown to OD600 of 0.8 in 10 mM $MgCl_2$). T1 seed is collected from these plants, and germinated on an agar-solidified medium containing (50 ug/ml Basta) or sprayed in soil (400 $\mu$g/ml Basta). Typically, 0.1% to 1.0% of the plants contain T-DNA inserts in a population of T1 transformants. Furthermore, the plants that survive on Basta selection are hemizygous for the T-DNA insertion and thus the Basta selectable marker.

Mutants blocked in growth or development are identified by examining T2 progeny using an embryo screen and recovering those plants that contained 25% aborted seeds. Using segregation analysis of T2 individuals, approximately one-third of the mutants are tagged.

Example 2

Embryo Screen for the Identification of Mutants Blocked in Early Development from Tagged Embryo-Lethal Lines 8388, 18048, and 16713

Essential genes are identified through the isolation of lethal mutants blocked in early development. Examples of lethal mutants include those blocked in the formation of the male or female gametes, embryo, or resulting seedling. Gametophytic mutants are found by examining T1 insertion lines for the presence of 50% aborted pollen grains or ovules. Embryo defective lethal mutants produce 25% defective seeds following self-pollination of T1 plants (see Errampalli et al. 1991, Plant Cell 3:149–157; Castle et al. 1993, Mol Gen Genet 241:504–514). Seedling lethal mutants segregate for 25% seedli ngs that exhibit a lethal phenotype.

The T1 line #8388 shows 250% defective seeds that contain embryos that are normal in size and shape, but completely lack normal pigmentation, i.e. they are albino. Similarly, defective seeds are normal in size and shape, and are white, rather than green, in mature siliques.

The T1 line #18048 shows 25% defective seeds that contain embryos that abort very early in development soon after fertilization.

The T1 line #16713 shows 25% defective seeds that contain embryos that abort very early in development soon after fertilization.

Example 3

Cosegregation Analysis for Tagged Embryo-Lethal Lines 8388,18048, and 16713

The linkage of the mutation to the T-DNA insert is established after identifying a transformed line segregating for a lethal phenotype of interest. A line segregating with a single functional insert will segregate for resistance in the ratio of 2:1 (resistance:sensitive) to the selectable marker Basta. In this case, one-quarter of the T2 progeny will fail to germinate due to embryo lethality, resulting in a reduction of the normal 3:1 ratio to 2:1. Each of the Basta resistant progeny are therefore heterozygous for the mutation if the T-DNA insert is causing the mutant phenotype. To confirm cosegregation of the T-DNA and the mutant phenotype, Basta resistant progeny are transplanted to soil and screened again for the presence of 25% aborted seeds.

For 8388, each of the 23 progeny examined contains approximately 25% aborted seeds with the expected phenotype. These results confirm that there is no evidence for recombination between the T-DNA and the mutation. Single plant southern blot analysis suggests that the T-DNA insertion in line #8388 con sists of a simple insertion.

For 18048, each of the 23 progeny examined contains approximately 25% aborted seeds with the expected phenotype. These results confirm that there is no evidence for recombination between the T-DNA and the mutation. Single plant Southern blot analysis suggests that the insertion in line #18048 consists of a at least three tandem T-DNA elements. Cosegregation analysis shows that Basta resistance and the mutant phenotype in line 18048 exhibit complete linkage in 94 selfed progeny from a selfed heterozygote.

For 16713, each of the 38 progeny examined contains approximately 25% aborted seeds with the expected phenotype. These results confirm that there is no evidence for recombination between the T-DNA and the mutation. Cosegregation analysis shows that Basta resistance and the mutant phenotype in line 16713 exhivit complete linkage in 38 selfed progeny from a selfed heterozygote.

Example 4a

Plasmid Rescue from Tagged Embryo-Lethal Line 8388

Arabidopsis genomic DNA is isolated as described Reiter et al in *Methods in Arabidopsis Research*, World Scientific Press (1992). Genomic DNA is digested with a restriction endonuclease and ligatcd overnight. After ligation, the DNA is transformed into competent *E. coli* strain XL-1 Blue, DH10B, DH5 alpha, or the like, and colonies are selected on semi-solid medium containing ampicillin. Resistant colonies are picked into liquid medium with ampicillin and grown overnight. Plasmid DNA is isolated and digested with the rescue enzyme and analyzed on agarose gels containing ethidium bromide for visualization. Plasmids that represent different size classes are sequenced using primers that flank the plant DNA portion of the rescue element and the sequence is analyzed to determine what portion is plant DNA and what gene has been disrupted.

One method of confirming that the disrupted gene is the cause of the mutant phenotype is to transform a wild-type form of the gene into the mutant plant. Alternatively, the mutant is phenocopied by specifically reducing expression of the disrupted gene in transgenic plants expressing an antisense version of the gene behind a synthetic promoter (Guyer et al. (1998) Genetics, 149: 633–639).

Example 4b

Plasmid Rescue from Tagged Embryo-Lethal Line 18048

Arabidopsis genomic DNA is isolated as described in Reiter et al in *Methods in Arabidopsis Research*, World Scientific Press (1992). Genomic DNA is digested with a restriction endonuclease and ligated overnight. After ligation, the DNA is transformed into competent *E. coli* strain XL-1 Blue, DH10B, DH5 alpha, or the like, and colonies are selected on semi-solid medium containing ampicillin. Resistant colonies are picked into liquid medium with ampicillin and grown overnight. Plasmid DNA is isolated and digested with the rescue enzyme and analyzed on agarose gels containing ethidium bromide for visualization. Plasmids that represent different size classes are sequenced using primers that flank the plant DNA portion of the rescue element and the sequence is analyzed to determine what portion is plant DNA and what gene has been disrupted.

One method of confirming that the disrupted gene is the cause of the mutant phenotype is to transform a wild-type form of the gene into the mutant plant. Alternatively, the mutant is phenocopied by specifically reducing expression of the disrupted gene in transgenic plants expressing an antisense version of the gene behind a synthetic promoter (Guyer et al. (1998) Genetics, 149: 633–639).

DNA flanking the borders of line #18048 is isolated using modifications to the Genome Walker kit (CLONTECH Laboratories, Palo Alto, Calif.). In general, DNA from the heterozygous mutant is digested with several different blunt cutting restriction endonucleases in parallel. The protocol is modified by using four enzymes that do not have a recognition site in the T-DNA insertion element. Adapters are ligated onto the ends of restriction fragments. These separate digests and ligations constitute different libraries of adapter-ligated restriction fragments. The libraries are used as template DNA in a PCR-based approach to specifically amplify the borders flanking the T-DNA insert. To achieve specificity, nested PCR primers from either the right border or left border of the T-DNA are used in combination with adapter PCR primers in a series of PCR reaction reactions to amplify plant DNA flanking the T-DNA insertion. The PCR products are sequenced, or cloned and sequenced.

Example 4c

Border Rescue from Tagged Embryo-Lethal Line 16713

Arabidopsis genomic DNA is isolated as described in Reiter et al in *Methods in Arabidoysis Research*, World Scientific Press (1992), DNA flanking the borders of line #16713 is isolated using TAIL PCR. A series of 12 TAIL PCR reactions are performed on DNA from line #16713; 6 arbitrary degenerate primers (CA50 primer: 5' NGT CGA SWG ANA WGA A 3': SEQ ID NO:9 (128-fold, AD2 from Liu et al. (1995) The Plant Journal, 8: 457–463); CA51 primer: 5' TGW GNA GSA NCA SAG A 3': SEQ ID NO:10 (128-fold derivative of AD1 from Liu and Whittier (1995) Genomics, 25: 674–681); CA52 primer: 5' AGW GNA GWA NCA WAG G 3': SEQ ID NO:11(128-fold, AD2 from Liu and Whittier (1995) Genomics, 25:674–681); CA53 primer: 5' STT GNT AST NCT NTG C 3': SEQ ID NO:12 (256-fold, AD5 from Tsugeki et al. (1996) The Plant Journal, 10: 479–489); CA54 primer: 5' NTC GAS TWT SGW GTT 3': SEQ ID NO:13 (64-fold, AD1 from Liu et al. (1995) The Plant Journal, 8: 457–463); and CA55 primer: 5' WGT GNA GWA NCA NAG A 3': SEQ ID NO:14 (256-fold, AD3 from Liu et al. (1995) The Plant Journal, 8: 457–463) are used in combination with two sets of nested, and T-DNA specific primers for the right border (CA66 primer: 5' ATT AGG CAC CCC AGG CTT TAC ACT TTA TG 3': SEQ ID NO:15 (pCSA104 right border primary primer); CA67 primer: 5' GTA TGT TGT GTG GAA TTG TGA GCG GAT AAC 3': SEQ ID NO:16 (pCSA104 right border secondary primer); and CA68 primer: 5' TAA CAA TTT CAC ACA GGA AAC AGC TAT GAC 3': SEQ ID NO:17 (pCSA104 right border tertiary primer) as well as for the left border (JM33 primer: 5' TAG CAT CTG AAT TTC ATA ACC AAT CTC GAT ACA C 3': SEQ ID NO:18 (pCSA104 left border tertiary primer; JM34 primer: 5' GCT TCC TAT TAT ATC TTC CCA AAT TAC CAA TAC A 3': SEQ ID NO:19 (pCSA104 left border secondary primer); and JM35 primer: 5' GCC TTT TCA GAA ATG GAT AAA TAG CCT TGC TTC C 3': SEQ ID NO:20 (pCSA104 left border primary primer) of the T-DNA region ofpCSA104.

A total of seven products are obtained from the left border and eight products from the right border. PCR primers specific to the genomic region are then designed and used to confirm the border products obtained by TAIL PCR.

Example 5a

Sequence Analysis of Tagged Embryo-Lethal Line #8388 From the Insertional Mutant Collection Analysis of *Arabidopsis thaliana* genomic DNA sequence flanking the right border region of the T-DNA insert in line 8388 reveals a single exon open reading frame of 1,656 bp (SEQ ID NO:1). *Arabidopsis thaliana* genomic DNA flanking the T-DNA border is identical to the ESTs 166E6T7 (Genbank Accession #R30603) and 203E14T7 (Genbank Accession #H77096) and to portions of the genomic survey sequences T19C17TR (Genbank Accession #B28763) F13K23-Sp6 (Genbank Accession #B10372). Sequence of the open reading frame used as a BLASTX 2.0.7 query yielded the hits listed in the chart below.

| Genbank Accession # | % Identity | % Similarity | E Value |
|---|---|---|---|
| 90965[1] | 29 | 49 | 100E-49 |
| 1170507[2] | 27 | 47 | 300E-43 |
| AB001488_42[3] | 30 | 49 | 200E-48 |

[1]eIF-4A I from mouse (note: human, rabbit, and mouse eIF4A I are identical at the amino acid level, and therefore give identical scores)
[2]eIF-4A-3 from *Nicotiana plumbaginifolia*.
[3]ATP dependent RNA helicase DEAD homolog from *Bacillus subtilis*.

Using GAP (Seq Web version 10.0, GCG), pairwise comparisons of the protein sequence (SEQ ID NO:2) and input sequences shown below give a measure of similarity between SEQ ID NO:2 and the identical sequences, and they are summarized below.

| GenPept Accession # | % Identity | % Similarity |
|---|---|---|
| AAD20136[4] | 36.554 | 46.214 |
| S00986[1] | 31.852 | 46.173 |
| 1170507[2] | 29.923 | 44.501 |
| BAA19295[3] | 35.250 | 45.750 |

[1]eIF-4A I from mouse (note: human, rabbit, and mouse eIF4A I are identical at the amino acid level, and therefore give identical scores)
[2]eIF-4A-3 from *Nicotiana plumbaginifolia*.
[3]ATP dependent RNA helicase DEAD homolog from *Bacillus subtilis*.
[4]autoaggregation-mediating protein from *Lactobacillus reuteri*..

Example 5b

Sequence Analysis of Tagged Embryo-Lethal Line #18048 From the Insertional Mutant Collection In the case of line #18048, there are multiple, tandemly arrayed T-DNA elements with left border sequences facing outward into plant DNA on both sides of the insert. Using the GenomeWalker strategy and left border-specific primers, a set of four independent PCR fragments are obtained and sequenced. Each of these four fragments shares sequence identity to the same region of a sequenced BAC clone (T30D6, accession number AC006439). Note that the BAC clone sequence is completed and is annotated by the public Arabidopsis Genome Sequencing project. Our sequences, both genomic and cDNA, match the predicted sequence exactly. Comparison of the recovered fragments with the T30D6 BAC clone sequence reveals that a 13 base deletion occurred upon insertion of the T-DNA in this mutant.

Analysis of the DNA sequence from the recovered borders reveals a high degree of homology to members of the ADP ribosylation factor (Arf) family of genes. Further inspection of recovered border fragments reveals that the T-DNA has inserted in the middle of the coding region for a gene that encodes a protein with greater than 60% identity to Arf-like (Arl) proteins from Drosophila, human, and rat. Sequence of the protein (SEQ ID NO:6) used as a BLASTP 2.0.8 query yields the hits listed in the chart below.

| Genbank Accession # | % Identity | % Similarity | E Value |
|---|---|---|---|
| NP_001658[1] | 64 | 85 | 7.00E-67 |
| O08697[2] | 62 | 82 | 1.00E-66 |
| Q06849[3] | 61 | 79 | 5.00E-64 |
| CAA90353[4] | 51 | 69 | 3.00E-55 |
| Q09767[5] | 49 | 71 | 1.00E-48 |
| P49076[6] | 47 | 65 | 9.00E-40 |
| AAD17207[7] | 47 | 65 | 1.00E-39 |

[1]pARL2 protein from human
[2]ARL2_RAT protein from rat

-continued

| Genbank Accession # | % Identity | % Similarity | E Value |
|---|---|---|---|

[3]ARL2_DROME protein from Drosophila
[4]ARFM_CAEEL protein from C. elegans
[5]ARL_SCHPO protein from S. pombe
[6]ARF_MAIZE protein from maize
[7]GMARF protein from soybean Using GAP (Seq Web version 10.0, GCG), pairwise comparisons of the protein sequence (SEQ ID NO:6) and input sequences shown below give a measure of similarity between SEQ ID NO:6 and the indicated sequences, and they are summarized below.

| Genbank Accession # | % Identity | % Similarity |
|---|---|---|
| NP_001658[1] | 64.130 | 72.283 |
| O08697[2] | 63.043 | 72.283 |
| Q06849[3] | 61.413 | 70.652 |
| CAA90353[4] | 55.676 | 68.108 |
| Q09767[5] | 48.370 | 66.304 |
| P49076[6] | 48.876 | 60.112 |
| AAD17207[7] | 47.458 | 58.757 |

[1]pARL2 protein from human
[2]ARL2_RAT protein from rat
[3]ARL2_DROME protein from Drosophila
[4]RFM_CAEEL protein from C. elegans
[5]ARL_SCHPO protein from S. pombe
[6]ARF_MAIZE protein from maize
[7]GMARF protein from soybean Example 5c Sequence Analysis of Tagged Embryo-Lethal Line #16713 From the Insertional Mutant Collection The sequence of the TAIL PCR border products matches the sequence from the P1 clone MIF21. All 15 TAIL PCR border products represent the same genomic region of the P1 clone MIF21 (Accession #AB023239). Further analysis of these products reveals a 44 base pair deletion that occurred upon T-DNA insertion in line #16713, corresponding to base number 46123 through 46167, of the P1 clone MIF21.

Analysis of the DNA sequence from the recovered borders reveals a high degree of homology to members of the acetoacetyl coA thiolase genes. Further inspection of recovered border fragments reveals that the T-DNA has inserted in the middle of the coding region for a gene that encodes a protein with greater than 50% identity to acetoacetyl-CoA thiolase proteins from radish, corn, yeast, human, and rat. Using GAP (Seq Web version 10.0, GCG), pairwise comparisons of the protein sequence (SEQ ID NO:8) and input sequences shown below give a measure of similarity between SEQ ID NO:8 and the indicated sequence; and are summarized below.

| Genbank Accession # | % Identity | % Similarity |
|---|---|---|
| CAA55006[1] | 93.0 | 94.0 |
| AAD44539[2] | 74.0 | 82.4 |
| P41338[3] | 54.9 | 64.3 |
| BAA14278[4] | 51.5 | 60.9 |
| BAA03016[5] | 51.6 | 61.2 |

-continued

| Genbank Accession # | % Identity | % Similarity |
|---|---|---|
| AAA82403[6] | 49.0 | 57.1 |
| Q46939[7] | 45.6 | 55.9 |

[1]cytosolic acetoacetyl-coenzyme A thiolase from radish
[2]acetoacetyl CoA thiolase from maize
[3]acetoacetyl CoA thiolase from S. cerevisiae
[4]mitochondrial acetoacetyl-coenzyme A thiolase from human
[5]mitochondrial acetoacetyl-CoA thiolase from rat
[6]acetyl-CoA thiolase from C. elegans
[7]acetoacetyl-CoA thiolase from E. coli Example 5d Sequence Analysis of Tagged Seedling—Lethal Line #4144 From the T-DNA Mutagenized Population of Arabidopsis The plasmid rescue technique is used to molecularly clone Arabidlopsis flanking DNA from one or both sides of the T-DNA insertion(s). Plasmnids obtained in this manner are analyzed by restriction enzyme digestion to sort the plasmids into classes based on their digestion pattern. For each class of plasmid clone, the DNA sequence is determined. The resulting sequences are analyzed for the presence of non-T-DNA vector sequence. The plasmids recovered from the plasmid rescue protocol are sequenced using the slp346 primer (5' GCGGACATCTACATTTTTGA 3'; SEQ ID NO:26). Primer slp346 provides information on the flanking sequence immediately adjacent to the left T-DNA border. The plasmid rescue is validated via PCR of template genomic DNA from a heterozygote for the 4144 insertion mutation. The experiment uses a primer anchored in the predicted flanking sequence and the sip346 primer. Finding a PCR product of the appropriate size, based on the sequence of the plasmid rescue clone confirms a valid rescue.

The sequence obtained from the above clone is used in BLASTx and BLASTn searches against nucleotide databases. (Altschul et al. (1990) J Mol. Biol. 215:403–410; Altschul et al. (1997) Nucleic Acids Res. 25:3389–3402). The BLASTx results show that the translated plant flanking sequence shows similarity to the chloroplast ATP synthase delta chain from a number of organisms including spinach (SWISS PROT P11402), pea (SWISS PROT Q02758), millet (SWISS PROT Q07300), corn (PIR S43729), and tobacco (SWISS PROT P32980). The BLASTn results show the rescued flanking sequence to be identical to preliminary genomic sequence CSHL076 T25P22-99.03.10-68148.seq. (found at http://genome-www2.stanford.edu/cgi-bin/AtDB/getseq?database=cshlprel&item=CSHL076). The region of genomic DNA where the T-DNA insertion occurred includes bases #26,159 through #27,088 of the annotated CSHL076 T25P22–99.03.10–68148. sequence, resulting in a seventy nine-base deletion. The BLASTn results also show the rescued flanking sequence is similar to Arabiclopsis sequences from EST cDNA clones 71D2T7 (GenBank T45339), GBGe205 (GenBank Z26062 and Z28994), 174J16T7 (GenBank AA712658), 116O10T7 (GenBank T42797), and 121M24T7 (GenBank AA721953). From our own sequencing of EST 71D2, we identify the ORF of the cDNA sequence as that in SEQ ID NO:21. These data indicate that there are no introns in this gene.

The sequence obtained from the above clone is used in GAP searches against protein databases, and the following results are obtained. B. rapa (GenBank #BAA11390): 89.5%, spinach (SWISS PROT #P11402): 54.1%, pea (SWISS PROT #Q02758): 57.9%, tobacco (SWISS PROT

P32980): 63.9%, millet (SWISS PROT #Q07300): 49.4%, and maize (PIR #S43729): 58.3%. The sequence obtained from the above clone is used in GAP searches against nucleotide databases, and the following result is obtained: B. rapa (DDBJ #D78493): 82.1%.

Example 6a

Isolation and Identification of 8388 cDNA Coding Region

The cDNA clone 166E6 is obtained from the Michigan State University EST collection (Newman et al. (1994) Plant Physiol. 106:1241–1255). It is picked from that collection and the insert sequenced completely (SEQ ID NO:3). The sequence from that cDNA clone is identical to the sequence derived from plasmid rescue from the 8388 line (SEQ ID NO:1), excepting that there are 5 silent nucleotide substitutions due to allelic variation in the open reading frame of the two sequences. The substitutions are a C at base 282 of SEQ ID NO:1 to a G at base 553 of SEQ ID NO:3; a G at base 1011 of SEQ ID NO:1 to a T at base 1282 of SEQ ID NO:3; a C at base 1188 of SEQ ID NO:1 to a T at base 1459 of SEQ ID NO:3; C at base 1404 of SEQ ID NO:1 to a T at base 1675 of SEQ ID NO:3; a G at base 1413 of SEQ ID NO:1 to a T at base 1684 of SEQ ID NO:3. These silent substitutions do not effect the polypeptides encoded by SEQ ID NO:1 or SEQ ID NO:3; they are identical.

Example 6b

Isolation and Identification of 18048 cDNA Coding Region

A cDNA fragment corresponding to the coding region of the 18048 gene is amplified with primers from the putative coding region of this gene (SEQ ID NO:5). These primers are designed using the alignments of deduced peptides from ORF's in the genomic DNA with the Arl proteins from Drosophila, human, rat and yeast. The deduced polypeptide encoded by the 18048 gene is shown in SEQ ID NO:6.

Southern blot analysis shows that the 18048 gene is single copy in Arabidopsis, and is disrupted by a T-DNA insertion in the mutant line examined. In addition, northern blot analysis reveals that the 18048 gene from Arabidopsis is expressed in vegetative tissues of young seedlings and four-week-old plants. Because the 18048 gene is expressed in vegetative tissues, the function of this gene is likely to be essential throughout the life cycle, as well as in early embryo development. Therefore, chemicals that inhibit 18048-gene function are likely to be lethal when applied to plants.

Example 6c

Isolation and Identification of 16713 cDNA Coding Region

A cDNA fragment corresponding to the coding region of the 16713 gene is cloned by PCR from the pFL61 (Minet et al. (1992) Plant Journal, 2:417–422) cDNA library (SEQ ID NO:7). The deduced polypeptide encoded by the 16713 gene is shown in SEQ ID NO:8.

Northern blot analysis reveals that the 16713 gene from Arabidopsis is expressed in vegetative tissues of young seedlings and four-week-old plants. Because the 16713 gene is expressed in vegetative tissues, the function of this gene is likely to be essential throughout the life cycle, as well as in early embryo development. Therefore, chemicals that inhibit 16713-gene function are likely to be lethal when applied to plants.

Example 7a

Expression of Recombinant 8388 Protein in Heterologous Expression Systems

The coding region of the protein, corresponding to the cDNA clone SEQ ID NO:1, is subcloned into previously described expression vectors, and transformed into E. coli using the manufacturer's conditions. Specific examples include plasmids such as pBluescript (Stratagene, La Jolla, Calif.), the pET vector system (Novagen, Inc., Madison, Wis.) pFLAG (International Biotechnologies, Inc., New Haven, Conn.), and pTrcHis (Invitrogen, La Jolla, Calif.). E. coli is cultured, and expression of the 8388 activity is confirmed. Alternatively, eukaryotic expression systems such as cultured insect cells infected with specific viruses may be preferred. Examples of vectors and insect cell lines are described previously. Protein conferring 8388 activity is isolated using standard techniiques.

Example 7b

Expression of Recombinant 18048 Protein in Heterologous Expression Systems

The coding region of the protein, corresponding to the cDNA clone SEQ ID NO:5, is subcloned into previously described expression vectors, and transformed into E. coli using the manufacturer's conditions. Specific examples include plasmids such as pBluescript (Stratagene, La Jolla, Calif.), the pET vector system (Novagen, Inc., Madison, Wis.) pFLAG (International Biotechnologies, Inc., New Haven, Conn.), and pTrcHis (Invitrogen, La Jolla, Calif.). E. coli is cultured, and expression of the 18048 activity is confirmed. Alternatively, eukaryotic expression systems such as cultured insect cells infected with specific viruses may be preferred. Examples of vectors and insect cell lines are described previously. Protein conferring 18048 activity is isolated using standard techniques.

Example 7c

Expression of Recombinant 16713 Protein in Heterologous Expression Systems

The coding region of the protein, corresponding to the cDNA clone SEQ ID NO:7, is subcloned into previously described expression vectors, and transformed into E. coli using the manufacturer's conditions. Specific examples include plasmids such as pBluescript (Stratagene, La Jolla, Calif.), the pET vector system (Novagen, Inc., Madison, Wis.) pFLAG (International Biotechnologies, Inc., New Haven, Conn.), and pTrcHis (Invitrogen, La Jolla, Calif.). E. coli is cultured, and expression of the 16713 activity is confirmed. Alternatively, eukaryotic expression systems such as cultured insect cells infected with specific viruses may be preferred. Examples of vectors and insect cell lines are described previously. Protein conferring 16713 activity is isolated using standard techniques.

Example 7d

Expression of Recombinant 4144 Protein in Heterologous Expression Systems

The coding region of the protein, corresponding to the cDNA clone SEQ ID NO:21, is subcloned into an appropriate expression vector, and transformed into E. coli using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of the 4144 activity is confirmed. Protein conferring 4144 activity is isolated using standard techniques.

Example 8a

In vitro Recombination of 8388 Genes by DNA Shuffling

The nucleotide sequence shown in SEQ ID NO:1 is amplified by PCR. The resulting DNA fragment is digested by DNaseI treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, or into pESC vectors (Stratagene Catalog) for use in yeast; and transformed into a bacterial or yeast strain deficient in 8388 activity by electroporation using the Biorad Gene Pulser and the manufacturer's conditions. The transformed bacteria or yeast are grown on medium that contains inhibitory concentrations of an inhibitor of 8388 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

In a similar reaction, PCR-amplified DNA fragments comprising the *A. thaliana* 8388 gene encoding the protein and PCR-amplified DNA fragments comprising the 8388 gene from *E. coli* are recombined in vitro and resulting variants with improved tolerance to the inhibitor are recovered as described above.

Example 8b

In vitro Recombination of 18048 Genes by DNA Shuffling

The nucleotide sequence shown in SEQ ID NO:5 is amplified by PCR. The resulting DNA fragment is digested by DNase I treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, or into pESC vectors (Stratagene Catalog) for use in yeast; and transformed into a bacterial or yeast strain deficient in 18048 activity by electroporation using the Biorad Gene Pulser and the manufacturer's conditions. The transformed bacteria or yeast are grown on medium that contains inhibitory concentrations of an inhibitor of 18048 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

In a similar reaction, PCR-amplified DNA fragments comprising the *A. thaliana* 18048 gene encoding the protein and PCR-amplified DNA fragments comprising the 18048 gene from *E. coli* are recombined in vitro and resulting variants with improved tolerance to the inhibitor are recovered as described above.

Example 8c

In vitro Recombination of 16713 Genes by DNA Shuffling

The nucleotide sequence shown in SEQ ID NO:7 is amplified by PCR. The resulting DNA fragment is digested by DNase I treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, or into pESC vectors (Stratagene Catalog) for use in yeast; and transformed into a bacterial or yeast strain deficient in 16713 activity by electroporation using the Biorad Gene Pulser and the manufacturer's conditions. The transformed bacteria or yeast are grown on medium that contains inhibitory concentrations of an inhibitor of 16713 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

In a similar reaction, PCR-amplified DNA fragments comprising the *A. thaliana* 16713 gene encoding the protein and PCR-amplified DNA fragments comprising the 16713 gene from *E. coli* are recombined in vitro and resulting variants with improved tolerance to the inhibitor are recovered as described above.

Example 8d

In vitro Recombination of 4144 Genes by DNA Shuffling

The nucleotide sequence of SEQ ID NO:21 is amplified by PCR. The resulting DNA fragment is digested by DNaseI treatment essentially as described (Stemmer et al. (1994) PNAS 91: 10747–10751) and the PCR primers are removed from the reaction mixture. A PCR reaction is carried out without primers and is followed by a PCR reaction with the primers, both as described (Stemmer et al. (1994) PNAS 91: 10747–10751). The resulting DNA fragments are cloned into pTRC99a (Pharmacia, Cat no: 27-5007-01) for use in bacteria, and transformed into a bacterial strain deficient in 4144 activity by electroporation using the Biorad Gene Pulser and the manufacturer's conditions. The transformed bacteria are grown on medium that contains inhibitory concentrations of an inhibitor of 4144 activity and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined. Alternatively, the DNA fragments are cloned into expression vectors for transient or stable transformation into plant cells, which are screened for differential survival and/or growth in the presence of an inhibitor of 4144 activity. In a similar reaction, PCR-amplified DNA fragments comprising the Arabidopsis 4144 gene encoding the protein and PCR-amplified DNA fragments derived from or comprising another 4144 gene are recombined in vitro and resulting

Example 9a

In vitro Recombination of 8388 Genes by Staggered Extension Process

The *Arabiclopsis thaliana* 8388 gene encoding the 8388 protein and the *E. coli* 8388 homologous gene are each cloned into the polylinker of a pBluescript vector. A PCR reaction is carried out essentially as described (Zhao et al. (1998) Nature Biotechnology 16: 258–261) using the "reverse primer" and the "M13–20 primer" (Stratagene Catalog). Amplified PCR fragments are digested with appropriate restriction enzymes and cloned into pTRC99a and mutated 8388 genes are screened as described in Example 8a.

Example 9b

In vitro Recombination of 18048 Genes by Staggered Extension Process

The *Arabidopsis thaliana* 18048 gene encoding the 18048 protein and the *E. coli* 18048 homologous gene are each cloned into the polylinker of a pBluescript vector. A PCR reaction is carried out essentially as described (Zhao et al. (1998) Nature Biotechnology 16: 258–261) using the "reverse primer" and the "M13–20 primer" (Stratagene Catalog). Arnplified PCR fragments are digested with appropriate restriction enzymes and cloned into pTRC99a and mutated 18048 genes are screened as described in Example 8b.

Example 9c

In vitro Recombination of 16713 Genes by Staggered Extension Process

The *Arabidopsis thaliana* 16713 gene encoding the 16713 protein and the *E. coli* 16713 homologous gene are each cloned into the polylinker of a pBluescript vector. A PCR reaction is carried out essentially as described (Zhao et al. (1998) Nature Biotechnology 16: 258–261) using the "reverse primer" and the "M13–20 primer" (Stratagene Catalog). Amplified PCR fragments are digested with appropriate restriction enzymes and cloned into pTRC99a and mutated 16713 genes are screened as described in Example 8c.

Example 9d

In vitro Recombination of 4144 Genes by Staggered Extension Process

The Arabidopsis 4144 gene encoding the 4144 protein and another 4144 gene, or homologs thereof, or fragments thereof, are each cloned into the polylinker of a pBluescript vector. A PCR reaction is carried out essentially as described (Zhao et al. (1998) Nature Biotechnology 16: 258–261) using the "reverse primer" and the "M13–20 primer" (Stratagene Catalog). Amplified PCR fragments are digested with appropriate restriction enzymes and cloned into pTRC99a and mutated 4144 genes are screened as described in Example 8d.

Example 10

In vitro Binding Assays

Recombinant 8388, 18048, 16713, or 4144 protein is obtained, for example, according to Example 7a, 7b, 7c, or 7d, respectively. The protein is immobilized on chips appropriate for ligand binding assays using techniques which are well known in the art. The protein immobilized on the chip is exposed to sample compound in solution according to methods well know in the art. While the sample compound is in contact with the immobilized protein measurements capable of detecting protein-ligand interactions are conducted. Examples of such measurements are SELDI, biacore and FCS, described above. Compounds found to bind the protein are readily discovered in this fashion and are subjected to further characterization.

Example 11a

3-Ketoacyl-CoA Thiolase Activity Assay

The 3-ketoacyl-CoA thiolase activity assay is derived from Olesen et al. (1997) *FEBS Letters* 412, 138–140. The reaction volumes are preferably the ones described below, but can be varied depending on the experimental requirements. $0.01-1.0 \times 10^{-3}$ unit of an enzyme having 3-ketoacyl-CoA thiolase activity (one unit of activity is defined as the amount of enzyme required to produce 1 $\mu$mol/min of product) and 10–500 $\mu$M, but preferably 250 $\mu$M acetoacetyl-CoA (AcAc-CoA) are mixed in a final volume of 20 $\mu$L Tris-HCl (pH 7.0–9.0, but preferable 8.5) and 10–250 $\mu$M, but preferably 50 $\mu$M CoA. The production of acetyl-CoA is determined preferably according to Olesen et al. (1997) *FEBS Letters* 412, 138–140 by following the breakage of acetoacetyl-CoA (AcAc-CoA), measured by the decrease in absorption of the enol form at 302 nm. Alternatively, the formation of new thioester bonds can be measured by detecting increases in absorbance at 233 nm.

A follow-up HPLC assay is described in Antonenkov et al. (1997) J Biological Chemistry 272: 26023–26031, which is incorporated herein by reference.

Example 11b

RNA Helicase Assay

Assays for RNA helicase are described in the following references. The technique of fluorescence polarization is described in Spears et al. (1997) Analytical Biochemistry 247: 130–137. The technique of fluorescence energy transfer is described in Bjornson et al. (1994) Biochemistry 33: 14306–14316. The technique of fluorescence energy quenching is described in Houston et al. (1994) Proc. Natl. Acad. Sci. USA 91: 5471–5474. The technique of time resolved fluorescence energy transfer is described in Earnshaw et al. (1999) Journal of Biomolecular Screening 4: 239–248. All of the references described in this example are hereby incorporated by reference.

Example 12

Plastid Transformation

Transformation Vectors

For expression of a nucleotide sequence encoding a polypeptide having 8388, 18048, 16713, or 4144 activity encoding in plant plastids, plastid transformation vector pPH143 or pPH145 (WO 97/32011) is used; and this reference is incorporated herein by reference. The nucleotide sequence is inserted into pPH 143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Plastid Transformation

Seeds of *Nicotiana tabacum* c.v. 'Xanthi nc' are germinated seven per plate in a 1" circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) *Proc. Natl. Acad. Sci. USA* 90, 913–917). Bombarded seedlings are incubated on T medium for two days after which leaves are excised and placed abaxial side up in bright light (350–500 tmol photons/m$^2$/s) on plates of RMOP medium (Svab, Z., Hajdukiewicz, P. and Maliga, P. (1990) *Proc. Natl. Acad. Sci. USA* 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). Homoplasmic shoots are rooted aseptically on spectinomycin-containing MS/IBA medium (McBride, K. E. et al. (1994) *Proc. Natl. Acad. Sci. USA* 91, 7301–7305) and transferred to the greenhouse.

The above-disclosed embodiments are illustrative. This disclosure of the invention will place one skilled in the art in possession of many variations of the invention. All such obvious and foreseeable variations are intended to be encompassed by the appended claims.

What is claimed is:

1. A method of identifying a compound that binds to a plant polypeptide comprising SEQ ID NO:8, wherein said compound has herbicidal activity, comprising:

a) combining a polypeptide comprising SEQ ID NO:8 and a compound to be tested for the ability to bind to said polypeptide, under conditions conducive to binding;

b) selecting a compound identified in step (a) that binds to said polypeptide;

c) applying a compound selected in step (b) to a plant to test fcor herbicidal activity; and d) selecting a compound identified in step (c) that has herbicidal activity.

* * * * *